(12) United States Patent
Liu et al.

(10) Patent No.: US 10,399,978 B2
(45) Date of Patent: Sep. 3, 2019

(54) IMIDAZOPYRIDINE THIOGLYCOLIC ACID DERIVATIVES AS POTENT INHIBITORS OF HUMAN URATE TRANSPORTER 1

(71) Applicant: SHANDONG UNIVERSITY, Jinan (CN)

(72) Inventors: Xinyong Liu, Jinan (CN); Qing Meng, Jinan (CN); Peng Zhan, Jinan (CN); Zengjun Fang, Jinan (CN); Tong Zhao, Jinan (CN); Zhuosen Sun, Jinan (CN); Xiukun Sun, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 0 days.

(21) Appl. No.: 16/313,149

(22) PCT Filed: Sep. 2, 2016

(86) PCT No.: PCT/CN2016/097858
§ 371 (c)(1),
(2) Date: Dec. 25, 2018

(87) PCT Pub. No.: WO2018/023851
PCT Pub. Date: Feb. 8, 2018

(65) Prior Publication Data
US 2019/0225606 A1    Jul. 25, 2019

(30) Foreign Application Priority Data

Aug. 3, 2016  (CN) .......................... 2016 1 0629605

(51) Int. Cl.
*C07D 471/04*    (2006.01)
*A61P 19/06*    (2006.01)

(52) U.S. Cl.
CPC ............ *C07D 471/04* (2013.01); *A61P 19/06* (2018.01)

(58) Field of Classification Search
CPC .................................................... C07D 471/04
USPC .......................................................... 514/303
See application file for complete search history.

(56) References Cited

FOREIGN PATENT DOCUMENTS

WO    2018023851 A1 * 12/2018

* cited by examiner

*Primary Examiner* — Taofiq A Solola
(74) *Attorney, Agent, or Firm* — CBM Patent Consulting, LLC

(57) ABSTRACT

It relates to the imidazopyridine thioglycolic acid derivatives, the preparation, and use thereof. The invention contained imidazopyridine thioglycolic acid derivatives with the formula I or II or III. Also described here are preparation of imidazopyridine thioglycolic acid derivatives, pharmaceutical compositions comprising these compounds as therapy and prevention for gout.

7 Claims, No Drawings

IMIDAZOPYRIDINE THIOGLYCOLIC ACID DERIVATIVES AS POTENT INHIBITORS OF HUMAN URATE TRANSPORTER 1

FIELD OF THE INVENTION

This invention concerns imidazopyridine thioglycolic acid derivatives for treating hyperuricemia and gout. Also described herein are the preparation of these derivatives as potent inhibitors of human urate transporter 1, belonging to the field of organic synthesis and medicine technology.

BACKGROUND OF THE INVENTION

Uric acid, the final product of purine catabolism, is physiologically excreted in the urine. the source of uric acid includes endogenous and exogenous, of which endogenous uric acid accounts for approximately 80%, while the remainder is derived from dietary purines. Thus, overproduction of uric acid or insufficient renal elimination can cause hyperuricemia, which is generally defined as a serum level of uric acid of >6.0 mg/dL. Hyperuricemia can be asymptomatic, but when the blood uric acid concentration exceeds 6.8 mg/dL without treatment, monosodium urate crystallizes and is deposited in joints or surrounding tissues. This is the cause of gout, a severe disease that affects millions of people, especially adult men, worldwide. Both hyperuricemia and gout are associated with a range of chronic diseases, including hypertension, diabetes mellitus, metabolic syndrome, and renal and cardiovascular diseases.

Currently, there are several drug strategies to control urate levels. For a long time, the preferred drugs for clinical treatment of hyperuricemia were xanthine oxidase (XO) inhibitors. However, an appreciable proportion of patients do not respond well to XO inhibitors, due to serious side effects and the development of resistance. Thus, uricosuric drugs, which increase the urinary excretion of uric acid, are another option for patients who are intolerant of XO inhibitors.

Lesinuard is a new drug used for the treatment of gout. It was discovered fortuitously by Ardea Biosciences in 2008. Lesinurad was approved on 22 Dec. 2015 by US FDA, and was noted to increase the excretion of uric acid by inhibiting the uric acid salt transport protein 1 (URAT1).

On the other hand, lesinurad is associated with adverse events, such as headache and increased blood creatinine. Also, lesinurad should be used with caution in patients with liver and kidney insufficiency and cardiovascular disease. Therefore, there is still a need for better inhibitors targeting URAT1.

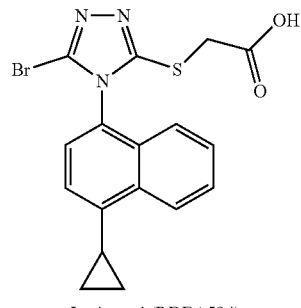

Lesinurad (RDEA594)

SUMMARY OF THE INVENTION

To overcome the disadvantages of Lesinurad, a series of imidazopyridine thioglycolic acid derivatives are disclosed and their preparation are described as follows, as well as an activity screening results and their applications as URAT1 inhibitors.

The technical scheme of the invention is as followed:

1. Imidazopyridine Thioglycolic Acid Derivatives

The invention provided a series of imidazopyridine thioglycolic acid derivatives, with structures of formula I, II or III.

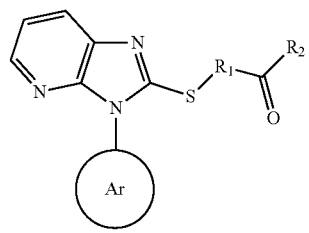

I

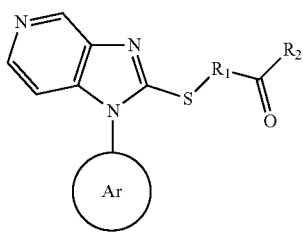

II

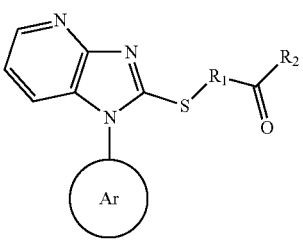

III wherein $R_1$ is —$CH_2$—, —*$CH_2(CH_3)$—, —$CH(CH_3)_2$— or —$CH_2CH_2CH_2$—;

R2 is —OH or —$OCH_2CH_3$;

Ar is an optionally substituted 1-naphthyl, 2,4,6-trimethylphenyl, 4-cyclopropyl-1-naphthyl or 2-naphthyl;

Preferably, compounds described here with structures of formula M1, M2, M3, M4, M5, M6, M7, M8, X1, X2, X3, X4, X5, X6, X7, X8, Q1, Q2, Q3, Q4, Q5, Q6, Q7, Q8, P1, P2, P3, P4, P5, P6, P7, P8, T1, T2, T3, T4, T5, T6, T7 and T8:

TABLE 1

Structures of Compounds M1~T8

| Num. | Structure |
|---|---|
| M1 | 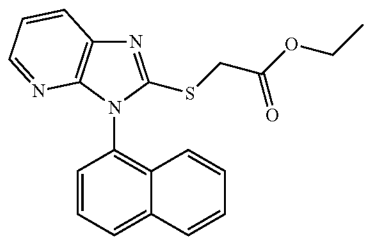 [SMILES: CCOC(=O)CSc1nc2cccnc2n1-c1cccc2ccccc12] |
| M2 | 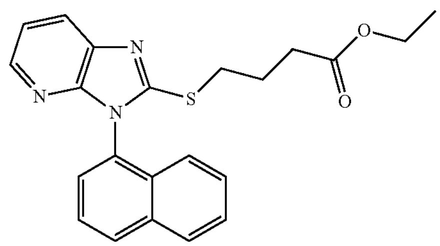 [SMILES: CCOC(=O)CCCSc1nc2cccnc2n1-c1cccc2ccccc12] |
| M3 | 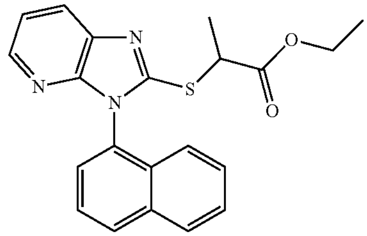 [SMILES: CCOC(=O)C(C)Sc1nc2cccnc2n1-c1cccc2ccccc12] |
| M4 | 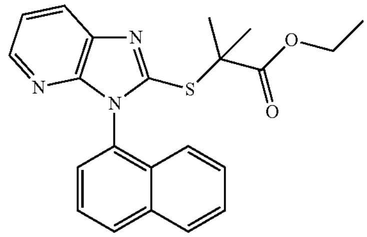 [SMILES: CCOC(=O)C(C)(C)Sc1nc2cccnc2n1-c1cccc2ccccc12] |
| M5 | 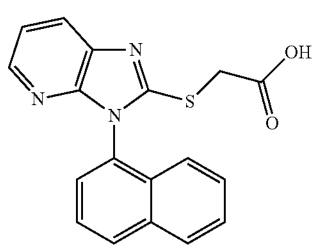 [SMILES: O=C(O)CSc1nc2cccnc2n1-c1cccc2ccccc12] |
| M6 | 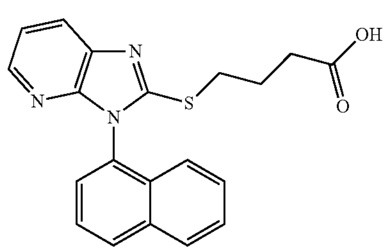 [SMILES: O=C(O)CCCSc1nc2cccnc2n1-c1cccc2ccccc12] |

TABLE 1-continued

Structures of Compounds M1~T8

| Num. | Structure |
|---|---|
| M7 | 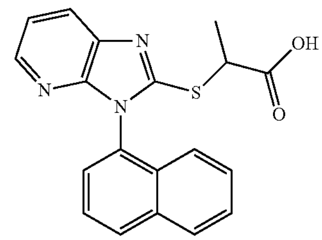 [SMILES: CC(Sc1nc2cccnc2n1-c1cccc2ccccc12)C(=O)O] |
| M8 | 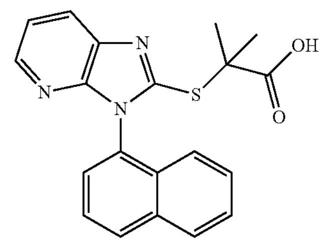 [SMILES: CC(C)(Sc1nc2cccnc2n1-c1cccc2ccccc12)C(=O)O] |
| X1 | 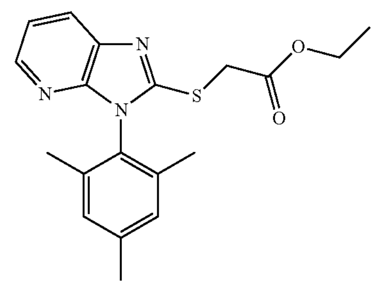 [SMILES: CCOC(=O)CSc1nc2cccnc2n1-c1c(C)cc(C)cc1C] |
| X2 | 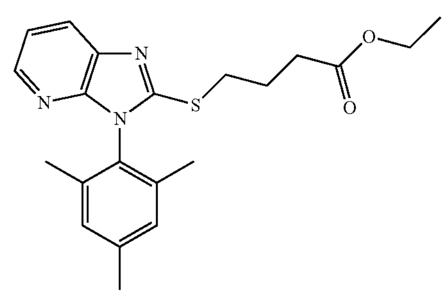 [SMILES: CCOC(=O)CCCSc1nc2cccnc2n1-c1c(C)cc(C)cc1C] |
| X3 | 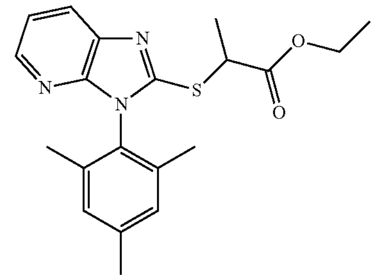 [SMILES: CCOC(=O)C(C)Sc1nc2cccnc2n1-c1c(C)cc(C)cc1C] |

TABLE 1-continued

Structures of Compounds M1~T8

| Num. | Structure |
|---|---|
| X4 | (imidazo[4,5-b]pyridine N-substituted with 2,4,6-trimethylphenyl; 2-S-C(CH3)2-C(O)O-ethyl) |
| X5 | (imidazo[4,5-b]pyridine N-substituted with 2,4,6-trimethylphenyl; 2-S-CH2-COOH) |
| X6 | (imidazo[4,5-b]pyridine N-substituted with 2,4,6-trimethylphenyl; 2-S-(CH2)3-COOH) |
| X7 | (imidazo[4,5-b]pyridine N-substituted with 2,4,6-trimethylphenyl; 2-S-CH(CH3)-COOH) |
| X8 | (imidazo[4,5-b]pyridine N-substituted with 2,4,6-trimethylphenyl; 2-S-C(CH3)2-COOH) |
| Q1 | (imidazo[4,5-b]pyridine N-substituted with 4-cyclopropylnaphthalen-1-yl; 2-S-CH2-C(O)O-ethyl) |
| Q2 | (imidazo[4,5-b]pyridine N-substituted with 4-cyclopropylnaphthalen-1-yl; 2-S-(CH2)3-C(O)O-ethyl) |
| Q3 | (imidazo[4,5-b]pyridine N-substituted with 4-cyclopropylnaphthalen-1-yl; 2-S-CH(CH3)-C(O)O-ethyl) |
| Q4 | (imidazo[4,5-b]pyridine N-substituted with 4-cyclopropylnaphthalen-1-yl; 2-S-C(CH3)2-C(O)O-ethyl) |

TABLE 1-continued
Structures of Compounds M1~T8
| Num. | Structure |
|---|---|
| Q5 | 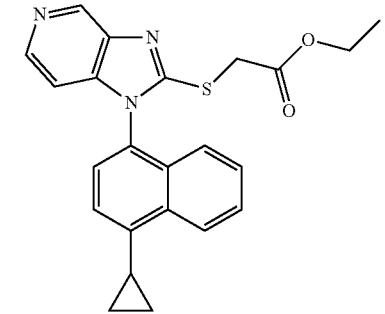 |
| Q6 | 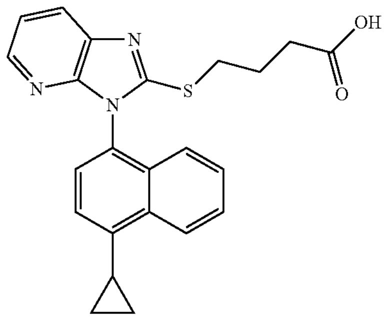 |
| Q7 | 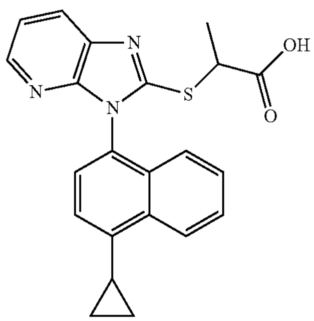 |
| Q8 | 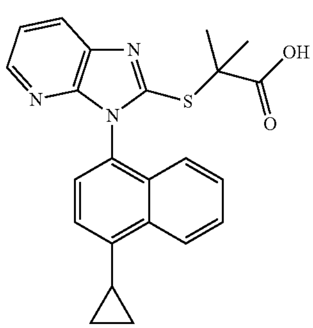 |
TABLE 1-continued
Structures of Compounds M1~T8
| Num. | Structure |
|---|---|
| P1 | 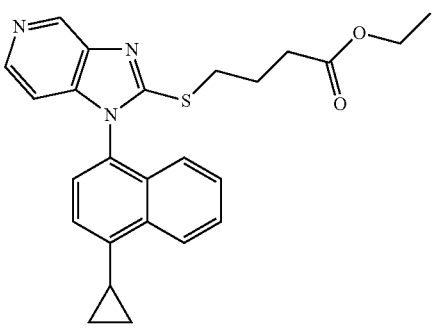 |
| P2 | 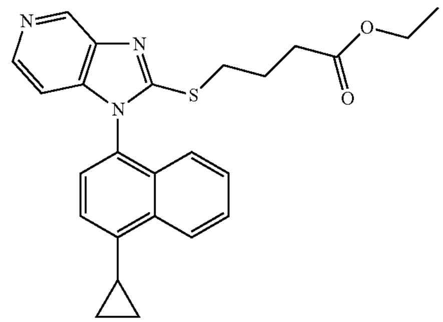 |
| P3 | 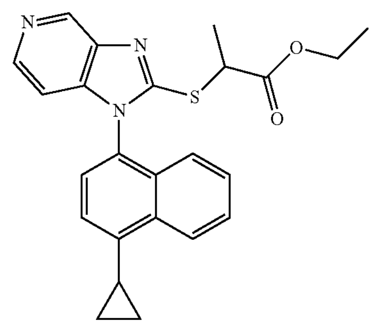 |
| P4 | 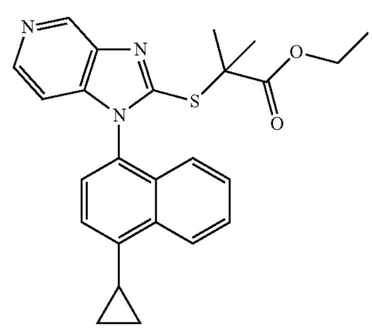 |

TABLE 1-continued
Structures of Compounds M1~T8
| Num. | Structure |
|---|---|
| P5 | 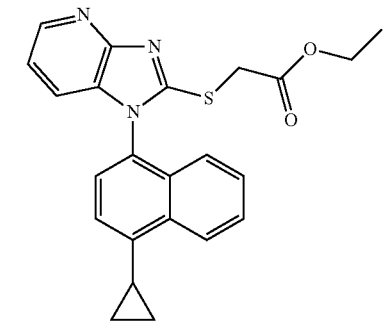 |
| P6 | 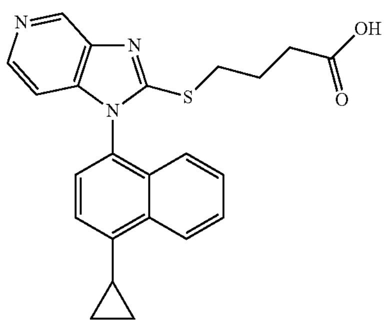 |
| P7 | 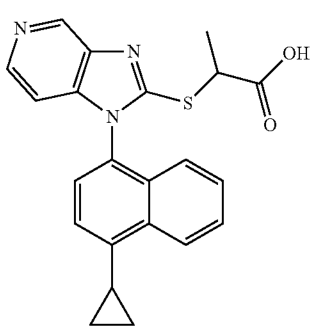 |
| P8 | 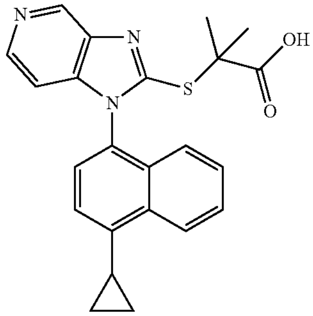 |
TABLE 1-continued
Structures of Compounds M1~T8
| Num. | Structure |
|---|---|
| T1 | 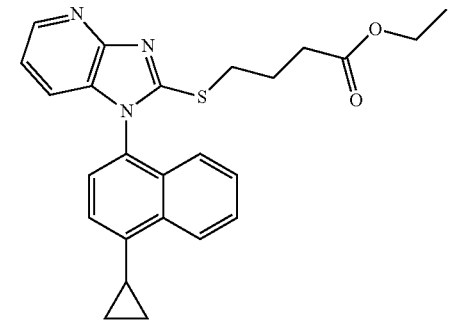 |
| T2 | 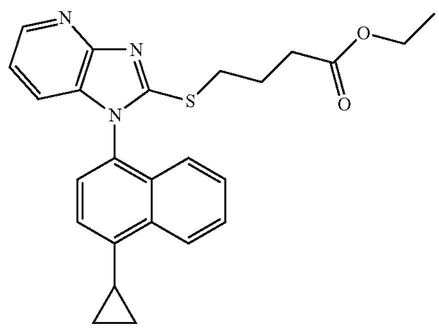 |
| T3 | 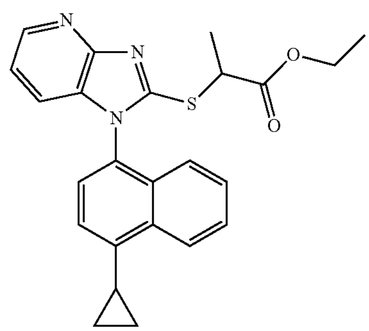 |
| T4 | 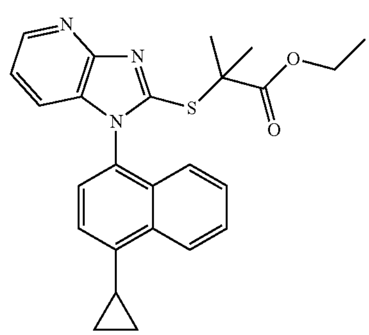 |

TABLE 1-continued

Structures of Compounds M1~T8

| Num. | Structure |
|---|---|
| T5 | 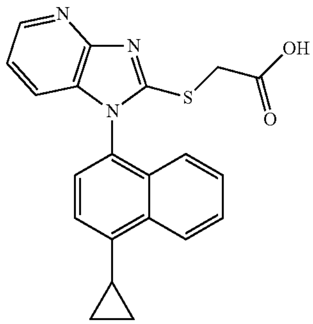 |
| T6 | 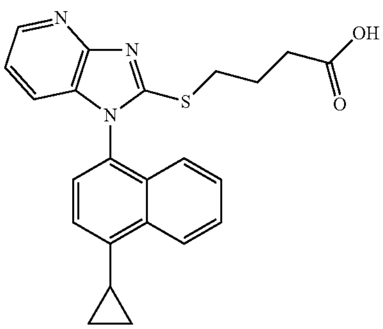 |
| T7 | 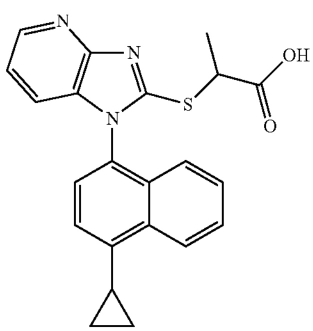 |
| T8 | 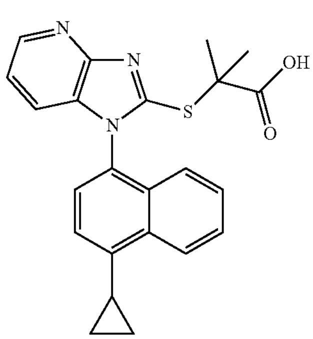 |

2. Preparation of Imidazopyridine Thioglycolic Acid Derivatives

The imidazopyridine thioglycolic acid derivatives were prepared as follows:

(1) Preparation of 3H-imidazole[4,5-b]pyridine Derivatives (Formula I)

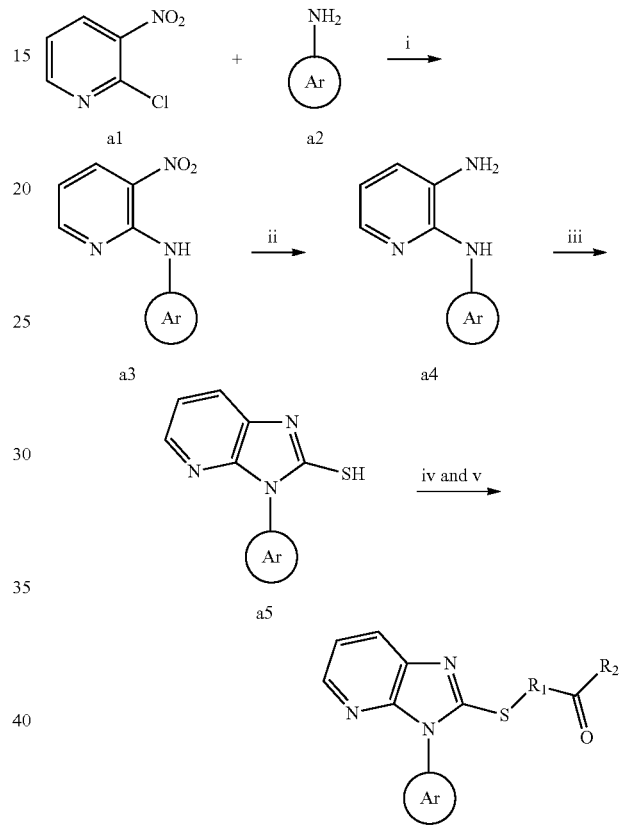

Scheme 1. Synthetic route to 3H-imidazole[4,5-b]pyridine derivatives (i) KF, 120° C.; (ii) Pd/C, H₂, EtOH; (iii) EtOCS₂K, NaHCO₃, H₂O, EtOH; (iv) ester, K₂CO₃, DMF; (v) LiOH, THF, EtOH.

3H-imidazole[4,5-b]pyridine derivatives were synthesized by well-established methods from commercially available 2-chloro-3-nitropyridine (a1). Treatment of a1 with naphthalen-1-amine afforded the intermediate a2. The nitro group of a2 was reduced using Pd/C to form a3, followed by cyclization with potassium ethylxanthate and sodium bicarbonate to afford a4. Nucleophilic substitution reactions of a4 afforded M1-M4, and hydrolysis with lithium hydroxide gave M5-M8. Compounds X1-X8 and Q1-Q8 were similarly prepared from M1-M8, except that 2,4,6-trimethylaniline and 4-cyclopropylnaphthalen-1-amine were used, respectively.

Wherein, the ester is selected from ethyl 4-bromobutyrate, ethyl 2-chloropropionate or ethyl 2-bromo-2-methylpropionate.

Wherein, the room temperature is represented 20-30° C.

While the $R_1$, $R_2$ and Ar are defined as formula I.

(2) Preparation of 1H-imidazole[4,5-c]pyridine Derivatives (Formula II)

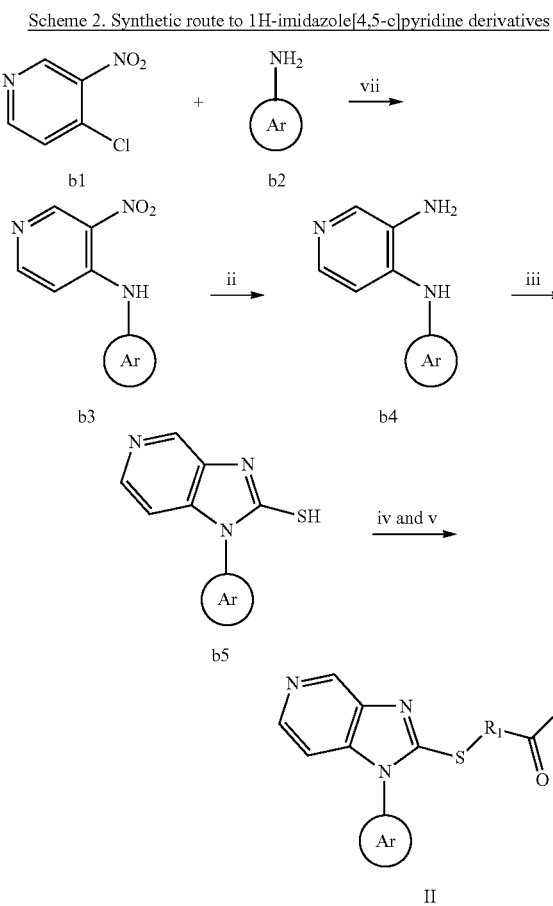

(vii) NaHCO₃, EtOH, 60° C.; (ii) Pd/C, H₂, EtOH; (iii) EtOCS₂K, NaHCO₃, H₂O, EtOH; (iv) ester, K₂CO₃, DMF; (v) LiOH, THF, EtOH.

Nucleophilic substitution of 4-chloro-3-nitropyridine (b1) with 4-cyclopropylnaphthalen-1-amine gave afforded the intermediate b2, which afforded P1-P8 via similar procedures to those shown in Scheme 1.

Wherein, the ester is selected from ethyl 4-bromobutyrate, ethyl 2-chloropropionate or ethyl 2-bromo-2-methylpropionate.

Wherein, the room temperature is represented 20-30° C.

While the $R_1$, $R_2$ and Ar are defined as formula II.

(3) Preparation of 1H-imidazole[4,5-b]pyridine Derivatives (Formula III)

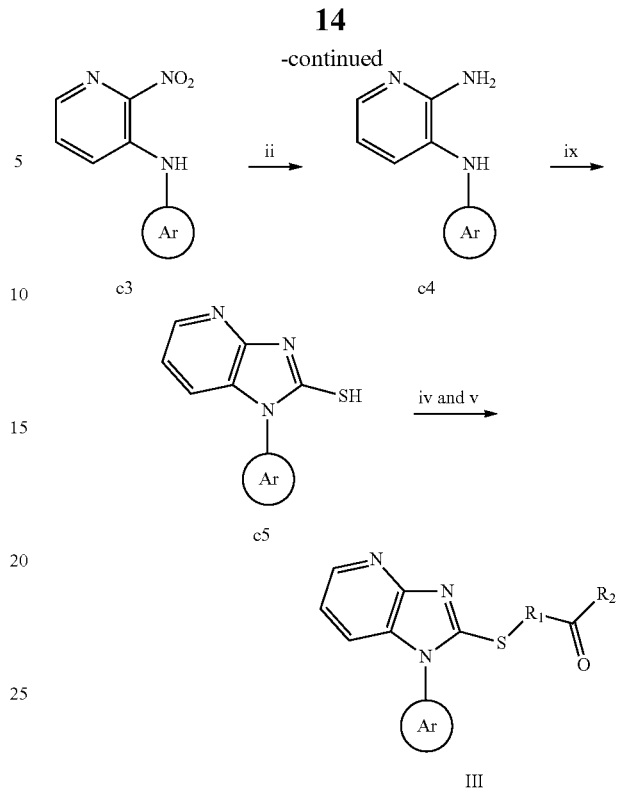

3-Chloro-2-nitropyridine (c1) was treated with 4-cyclopropyl-1-naphthylamine to afford intermediate c2 via Buchwald-Hartwig coupling reaction. Then, reduction in the presence of Pd/C gave c3, which was cyclized with 1,1'-thiocarbonyldiimidazole to give the key intermediate c4, followed by nucleophilic substitution and hydrolysis to provide T1-T8.

Wherein, the ester is selected from ethyl 4-bromobutyrate, ethyl 2-chloropropionate or ethyl 2-bromo-2-methylpropionate.

Wherein, the room temperature is represented 20-30° C.

While the $R_1$, $R_2$ and Ar are defined as formula Ill.

3. Activity of Reducing Blood Uric Acid and Use Thereof

All newly synthesized target compounds were primarily evaluated for their activities of reducing blood uric acid in vivo (mice). Benzbromarone and lesinurad were selected as positive control drugs. The results are summarized in Table 1.

The results showed that most of the novel compounds exhibited high potency in reducing blood uric acid. The URAT1 inhibition assay was performed as well, and some compounds exhibited more favorable URAT1 inhibition potency than lesinurad, so they can serve as lead compounds for further development.

Also described here are imidazopyridine thioglycolic acid derivatives used as URAT1 inhibitors, furthermore, these URAT1 inhibitors will be used as novel anti-gout agents.

Also described here are pharmaceutical composition comprising imidazopyridine thioglycolic acid derivatives, and with one or more kind of pharmaceutically acceptable carrier or excipient.

Also described here with novel imidazopyridine thioglycolic acid derivatives, a method of preparing these compounds, and their first application in the treatment of hyperuricemia and gout. Confirmed by experiments, the invented compounds are highly potent anti-gout agents with high value, which can be used as anti-gout drugs.

EXAMPLES

Selected examples are listed as follows, the invention includes these compounds disclosed herein but not confined to them.

Synthetic Routes:

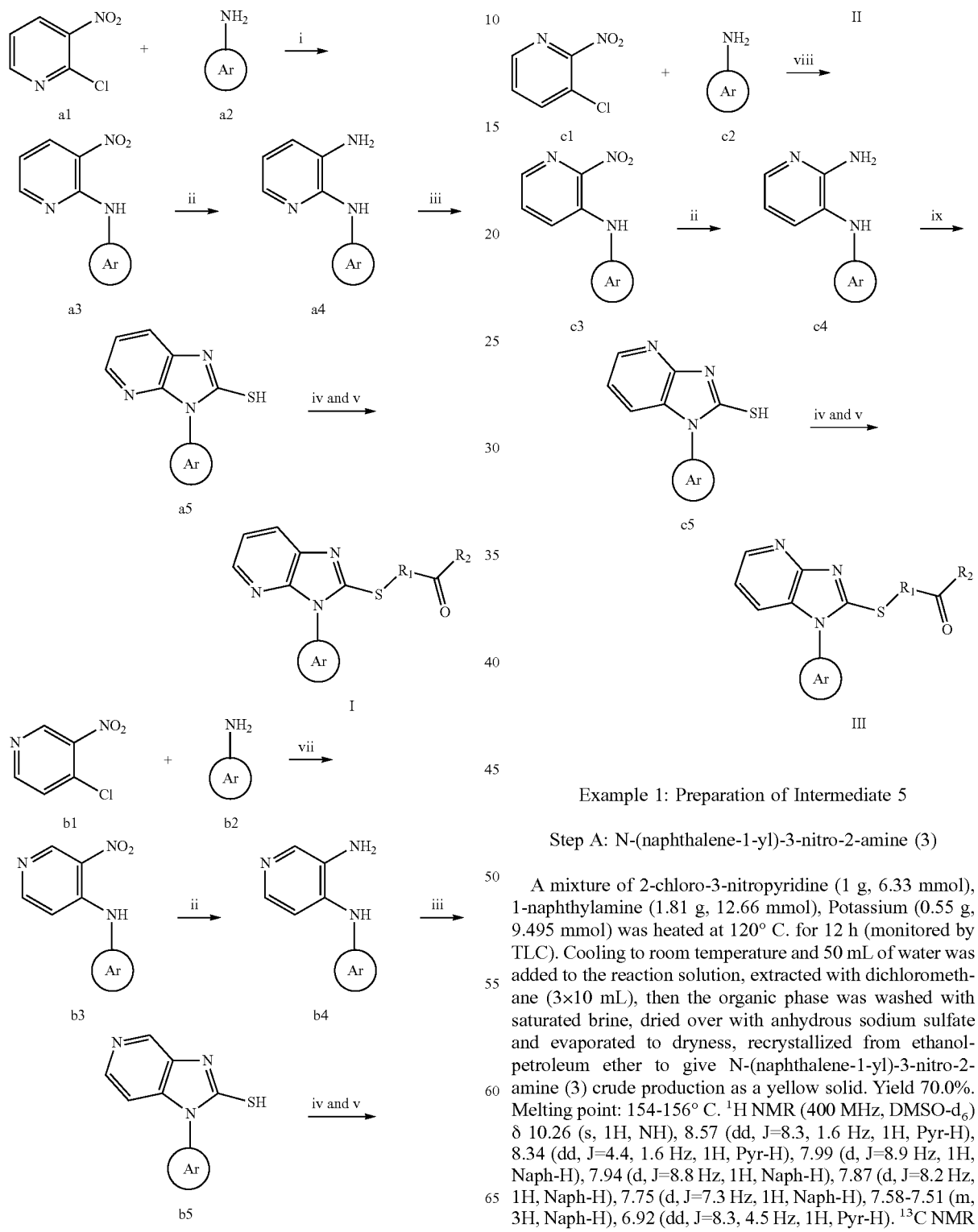

Example 1: Preparation of Intermediate 5

Step A: N-(naphthalene-1-yl)-3-nitro-2-amine (3)

A mixture of 2-chloro-3-nitropyridine (1 g, 6.33 mmol), 1-naphthylamine (1.81 g, 12.66 mmol), Potassium (0.55 g, 9.495 mmol) was heated at 120° C. for 12 h (monitored by TLC). Cooling to room temperature and 50 mL of water was added to the reaction solution, extracted with dichloromethane (3×10 mL), then the organic phase was washed with saturated brine, dried over with anhydrous sodium sulfate and evaporated to dryness, recrystallized from ethanol-petroleum ether to give N-(naphthalene-1-yl)-3-nitro-2-amine (3) crude production as a yellow solid. Yield 70.0%. Melting point: 154-156° C. $^1$H NMR (400 MHz, DMSO-$d_6$) δ 10.26 (s, 1H, NH), 8.57 (dd, J=8.3, 1.6 Hz, 1H, Pyr-H), 8.34 (dd, J=4.4, 1.6 Hz, 1H, Pyr-H), 7.99 (d, J=8.9 Hz, 1H, Naph-H), 7.94 (d, J=8.8 Hz, 1H, Naph-H), 7.87 (d, J=8.2 Hz, 1H, Naph-H), 7.75 (d, J=7.3 Hz, 1H, Naph-H), 7.58-7.51 (m, 3H, Naph-H), 6.92 (dd, J=8.3, 4.5 Hz, 1H, Pyr-H). $^{13}$C NMR (100 MHz, DMSO-$d_6$) δ 155.8, 151.7, 135.8, 134.8, 134.3, 129.8, 129.0, 128.7, 126.8, 126.6, 126.5, 126.2, 124.0, 123.1, 114.4. $C_{15}H_{11}N_3O_2$ (Exact Mass: 265.0851).

Step B: N2-(Naphthalen-1-yl)pyridine-2,3-diamine (4)

The intermediate 3 (1 g, 3.77 mmol) was dissolved in ethanol (30 mL) and palladium on carbon (0.1 g) was added to the solution. The mixture was stirred under the hydrogen atmosphere at the room temperature overnight (monitored by TLC). Then the mixture was filtered and concentrated under reduced pressure. Then recrystallized from ethyl acetate to obtain white solid $N_2$-(naphthalen-1-yl) pyridine-2,3-diamine (4). Yield 85.3%. Melting point: 171-172.5° C. $^1$H NMR (400 MHz, DMSO-$d_6$) δ 8.05 (d, J=7.8 Hz, 1H, Naph-H), 7.88 (d, J=8.9 Hz, 1H, Naph-H), 7.76 (s, 1H, NH), 7.57 (d, J=4.3 Hz, 1H, Pyr-H), 7.55 (d, J=3.3 Hz, 1H, Naph-H), 7.50-7.38 (m, 4H, Naph-H), 6.97 (dd, J=7.6, 1.3 Hz, 1H, Pyr-H), 6.64 (dd, J=7.6, 4.8 Hz, 1H, Pyr-H), 5.11 (s, 2H, $NH_2$). $^{13}$C NMR (100 MHz, DMSO-$d_6$) δ 145.5, 138.3, 135.3, 134.5, 132.9, 128.5, 128.0, 126.3, 126.0, 125.3, 123.5, 122.5, 120.5, 118.1, 116.6. $C_{15}H_{13}N_3$ (Exact Mass: 235.1109).

Step C: 3-(Naphthalen-1-yl)-3H-imidazo[4,5-b]pyridine-2-thiol (5)

The mixture of N2-(naphthalen-1-yl) pyridine-2,3-diamine (4) (0.61 g, 2.6 mmol), potassium ethylxanthogenate (0.5 g, 3.1 mmol) and sodium bicarbonate (0.05 g, 0.6 mmol) were dissolved in 48 mL mixed solvent (ethanol/water=5:1). The reaction was refluxed for 5 h, cooled to room temperature. A precipitate was formed by adding 10 mL water and 4 mL 2 M sodium hydroxide solution to the reaction solution, and filtered, then the pH of the filtrate was adjusted to 7 with 2M hydrochloric acid solution to give a precipitate which was filtered to afforded the 3-(Naphthalen-1-yl)-3H-imidazo[4,5-b]pyridine-2-thiol crude compound (5). white solid. Yield 92.8%. Melting point: 241-244° C. $^1$H NMR (400 MHz, DMSO-$d_6$) δ 13.37 (s, 1H, SH), 8.16 (d, J=8.3 Hz, 1H, Pyr-H), 8.10 (d, J=8.2 Hz, 1H, Naph-H), 8.01 (dd, J=5.0, 1.3 Hz, 1H, Pyr-H), 7.74-7.68 (m, 2H, Naph-H), 7.63-7.57 (m, 2H, Naph-H), 7.49-7.45 (m, 1H, Pyr-H), 7.28-7.24 (m, 2H, Naph-H). $^{13}$C NMR (100 MHz, DMSO-$d_6$) δ 171.6, 147.6, 142.9, 134.4, 131.6, 130.4, 130.1, 128.8, 128.5, 127.5, 126.9, 126.2, 125.46, 123.2, 119.7, 117.4. $C_{16}H_{11}N_3S$ (Exact Mass: 277.07).

Example 2: Preparation of M1

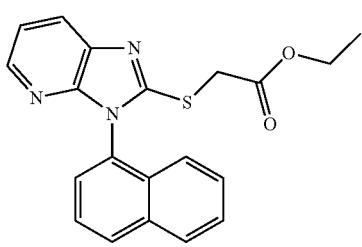

M1

Compound a5 was dissolved in DMF (10 mL) in the presence of potassium carbonate (0.31 g, 2.232 mmol), followed by addition of ethyl bromide (1.1 equiv). After stirring for 15 min, appropriate substituted ester (2.787 mmol) was added dropwise and stirred at room temperature for 4 h (monitored by TLC). The solvent was evaporated under reduced pressure and the residue was washed with ethyl acetate (30 mL) and saturated aqueous sodium chloride solution (3×10 mL). The organic layer was dried over anhydrous $Na_2SO_4$, filtered, and purified by flash column chromatography. The product was recrystallized from ethyl acetate (EA) to afford the target compounds M1. White solid, yield 67.1%, Melting point: 116.5-117° C. $^1$H NMR (400 MHz, DMSO-$d_6$) δ 8.25 (d, J=8.8 Hz, 1H, Pyr-H), 8.16 (d, J=8.2 Hz, 1H, Naph-H), 8.12-8.09 (m, 2H, Naph-H), 7.78-7.72 (m, 2H, Naph-H), 7.64 (t, J=8.0 Hz, 1H, Naph-H), 7.51 (t, J=8.0 Hz, 1H, Pyr-H), 7.31 (dd, J=7.9, 4.9 Hz, 1H, Naph-H), 7.09 (d, J=8.4 Hz, 1H, Pyr-H), 4.25 (d, J=2.6 Hz, 2H, $CH_2$), 4.13 (q, J=7.1 Hz, 2H, $CH_2$), 1.18 (t, J=7.1 Hz, 3H, $CH_3$). $^{13}$C NMR (100 MHz, DMSO-$d_6$) δ 168.5, 154.7, 150.9, 143.3, 135.4, 134.5, 131.0, 130.1, 130.1, 129.0, 128.1, 127.9, 127.4, 126.3, 125.8, 122.5, 119.1, 61.7, 33.4, 14.4. ESI-MS: m/z 364.1111 [M+H]+. $C_{20}H_{17}N_3O_2S$ (Exact Mass: 363.1041).

Example 3: Preparation of M2

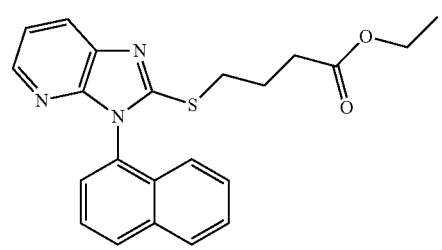

M2

Synthesized in a similar procedure with example 2 using ethyl 4-bromobutyrate as ester.

White solid, yield 72.3%, Melting point: 100-103° C. $^1$H NMR (400 MHz, DMSO-$d_6$) δ 8.22 (dd, J=6.7, 2.6 Hz, 1H, Pyr-H), 8.15-8.09 (m, 3H, Naph-H), 7.76-7.71 (m, 2H, Naph-H), 7.62 (t, J=7.9 Hz, 1H, Naph-H), 7.49 (t, J=7.7 Hz, 1H, Pyr-H), 7.30 (dd, J=7.9, 4.9 Hz, 1H, Naph-H), 7.05 (d, J=8.4 Hz, 1H, Pyr-H), 4.02 (q, J=7.1 Hz, 2H, $CH_2$), 3.37-3.33 (m, 2H, $CH_2$), 2.39 (t, J=7.3 Hz, 2H, $CH_2$), 1.99 (p, J=7.2 Hz, 2H, $CH_2$), 1.14 (t, J=7.1 Hz, 3H, $CH_3$). $^{13}$C NMR (100 MHz, DMSO-$d_6$) δ 172.6, 155.5, 150.9, 143.1, 135.5, 134.4, 130.8, 130.4, 130.2, 129.0, 128.1, 127.9, 127.3, 126.3, 125.6, 122.5, 119.0, 60.3, 32.6, 30.6, 24.7, 14.5. ESI-MS: m/z 392.1431 [M+H]+. $C_{22}H_{21}N_3O_2S$ (Exact Mass: 391.1354).

Example 4: Preparation of M3

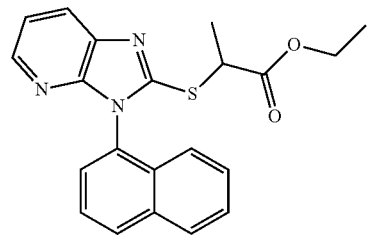

M3

Synthesized in a similar procedure with example 2 using ethyl 2-chloropropionate as ester.

White solid, yield 69.5%, Melting point: 144-145° C. $^1$H NMR (400 MHz, DMSO-d$_6$) δ 8.24 (dd, J=6.6, 2.6 Hz, 1H, Pyr-H), 8.16-8.11 (t, 3H, Naph-H), 7.77-7.70 (m, 2H, Naph-H), 7.64 (t, J=8.0 Hz, 1H, Naph-H), 7.50 (t, J=8.2 Hz, 1H, Pyr-H), 7.34-7.31 (m, 1H, Naph-H), 7.05 (t, J=7.7 Hz, 1H, Pyr-H), 4.77-4.70 (m, 1H, CH), 4.09 (q, J=7.1 Hz, 2H, CH$_2$), 1.57 (t, J=7.6 Hz, 3H, CH$_3$), 1.19-1.08 (m, 3H, CH$_3$). $^{13}$C NMR (100 MHz, DMSO-d$_6$) δ 171.3, 153.8, 150.7, 143.5, 135.4, 134.4, 131.0, 130.2, 130.1, 129.0, 128.1, 127.9, 127.4, 126.2, 125.9, 122.4, 119.2, 61.7, 43.6, 18.2, 14.3. ESI-MS: m/z 378.1275 [M+H]$^+$. C$_{21}$H$_{19}$N$_3$O$_2$S (Exact Mass: 377.1189).

Example 5: Preparation of M4

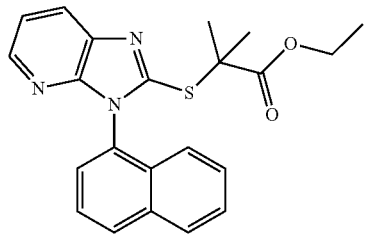

M4

Synthesized in a similar procedure with example 2 using ethyl 2-bromo-2-methylpropionate as ester.

White solid, yield 72.6%, Melting point: 135-136° C. $^1$H NMR (400 MHz, DMSO-d$_6$) δ 8.22 (d, J=8.1 Hz, 1H, Pyr-H), 8.15-8.09 (m, 3H, Naph-H), 7.74 (t, J=7.7 Hz, 1H, Naph-H), 7.68 (d, J=6.9 Hz, 1H, Naph-H), 7.63 (t, J=7.4 Hz, 1H, Naph-H), 7.50 (t, J=7.5 Hz, 1H, Pyr-H), 7.31 (dd, J=8.0, 4.8 Hz, 1H, Naph-H), 7.00 (d, J=8.4 Hz, 1H, Pyr-H), 4.12-4.10 (m, 2H, CH$_2$), 1.70 (s, 3H, CH$_3$), 1.63 (s, 3H, CH$_3$), 1.10 (t, J=7.1 Hz, 3H, CH$_3$). $^{13}$C NMR (100 MHz, DMSO-d$_6$) δ 172.8, 153.1, 150.1, 143.7, 135.4, 134.4, 130.8, 130.3, 130.2, 129.0, 128.1, 127.9, 127.4, 126.2, 126.1, 122.4, 119.2, 61.7, 53.1, 26.7 (2×C), 14.30. ESI-MS: m/z 392.1433 [M+H]$^+$. C$_{22}$H$_{21}$N$_3$O$_2$S (Exact Mass: 391.1354).

Example 6: Preparation of M5

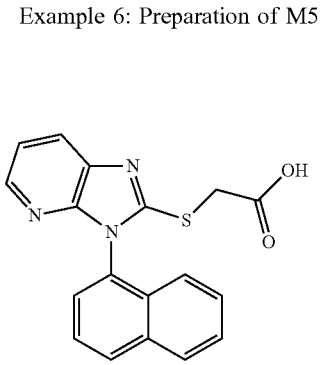

M5

M1 was dissolved in a mixed solution of 5 mL tetrahydrofuran and 5 mL ethanol. Lithium hydroxide (0.2 g, 8.26 mmol) was dissolved in a small amount of water and added dropwise to the solution. The mixture was stirred at 0° C. for 1 h. After the reaction was completed, the solvent was removed by rotary evaporation under reduced pressure. 10 mL of water was added to the residue, and 2M HCl solution was added dropwise to pH 3-4. After filtration, the ethanol was crystallized to obtain the target compound M5.

White solid, yield 87.1%. Melting point: 129-130° C. $^1$H NMR (400 MHz, DMSO-d$_6$) δ 8.24 (d, J=7.6 Hz, 1H), 8.10-8.16 (m, 3H), 7.80-7.69 (m, 2H), 7.64 (t, J=7.4 Hz, 1H), 7.50 (t, J=7.6 Hz, 1H), 7.31 (dd, J=7.8, 5.0 Hz, 1H), 7.09 (d, J=8.4 Hz, 1H), 4.19 (s, 2H, CH$_2$). $^{13}$C NMR (100 MHz, DMSO-d$_6$) δ 169.7, 155.1, 150.9, 143.2, 135.4, 134.5, 130.9, 130.2, 130.1, 129.0, 128.1, 127.9, 127.5, 126.3, 125.7, 122.6, 119.1, 34.0. ESI-MS: m/z 336.0800 [M+H]$^+$. C$_{18}$H$_{13}$N$_3$O$_2$S (Exact Mass: 335.0728).

Example 7: Preparation of M6

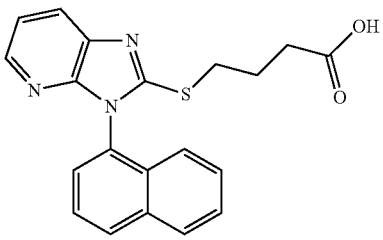

M6

Synthesized in a similar procedure with example 6.

White solid, yield 92.3%. Melting point: 129-130° C. $^1$H NMR (400 MHz, DMSO-d$_6$) δ 12.13 (s, 1H, OH), 8.22 (dd, J=6.6, 2.7 Hz, 1H, Pyr-H), 8.15-8.08 (m, 3H, Naph-H), 7.76-7.71 (m, 2H, Naph-H), 7.62 (t, J=7.9 Hz, 1H, Naph-H), 7.49 (t, J=8.1 Hz, 1H, Pyr-H), 7.30 (dd, J=8.0, 4.9 Hz, 1H, Naph-H), 7.05 (d, J=8.4 Hz, 1H, Pyr-H), 3.36-3.33 (m, 2H, CH$_2$), 2.33 (t, J=7.3 Hz, 2H, CH$_2$), 2.00-1.95 (m, 2H, CH$_2$). $^{13}$C NMR (100 MHz, DMSO-d$_6$) δ 174.2, 155.5, 150.9, 143.1, 135.5, 134.4, 130.8, 130.4, 130.2, 129.0, 128.1, 128.0, 127.3, 126.3, 125.6, 122.5, 119.0, 32.8, 30.7, 24.7. ESI-MS: m/z 364.1118 [M+H]$^+$. C$_{20}$H$_{17}$N$_3$O$_2$S (Exact Mass: 363.1041).

Example 8: Preparation of M7

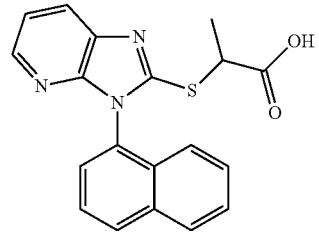

M7

Synthesized in a similar procedure with example 6.

White solid, yield 91.5%. Melting point: 110-112° C. $^1$H NMR (400 MHz, DMSO-d$_6$) δ 8.23 (d, J=7.5 Hz, 1H, Pyr-H), 8.15-8.11 (m, 3H, Naph-H), 7.76-7.70 (m, 2H, Naph-H), 7.63 (t, J=7.5 Hz, 1H, Naph-H), 7.52-7.47 (m, 1H, Pyr-H), 7.31 (dd, J=7.9, 4.9 Hz, 1H, Naph-H), 7.06 (d, J=8.5 Hz, 1H, Pyr-H), 4.68 (qd, J=7.2, 2.5 Hz, 1H, CH), 1.59 (dd, J=18.5, 7.2 Hz, 3H, CH$_3$). $^{13}$C NMR (100 MHz, DMSO-d$_6$) δ 172.8, 154.4, 150.7, 143.4, 135.5, 134.4, 130.9, 130.2, 129.0, 128.2, 127.9, 127.9, 127.4, 126.3, 125.8, 122.5, 119.1, 44.7, 18.9. ESI-MS: m/z 350.0954 [M+H]⁺. C₁₉H₁₅N₃O₂S (Exact Mass: 349.0885).

Example 9: Preparation of M8

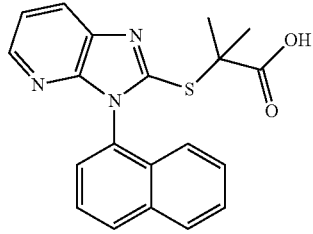

Synthesized in a similar procedure with example 6.

White solid, yield 93.7%. Melting point: 165-166° C. $^1$H NMR (400 MHz, DMSO-d₆) δ 8.22 (d, J=8.2 Hz, 1H, Pyr-H), 8.15-8.11 (m, 3H, Naph-H), 7.73 (t, J=7.7 Hz, 1H, Naph-H), 7.67 (dd, J=7.2, 1.1 Hz, 1H, Naph-H), 7.62 (t, J=8.0 Hz, 1H, Naph-H), 7.49 (t, J=8.1 Hz, 1H, Pyr-H), 7.33-7.30 (m, 1H, Naph-H), 7.00 (d, J=8.4 Hz, 1H, Pyr-H), 1.68 (s, 6H, 2×CH₃). $^{13}$C NMR (100 MHz, DMSO-d₆) δ 174.4, 153.4, 150.1, 143.7, 135.5, 134.4, 130.7, 130.5, 130.3, 128.9, 128.1, 128.0, 127.3, 126.2, 126.1, 122.4, 119.2, 53.9, 26.8, 26.8. ESI-MS: m/z 364.1116 [M+H]⁺. C₂₀H₁₇N₃O₂S (Exact Mass: 363.1041).

Example 10: Preparation of Intermediate 9

Step A: N-Mesityl-3-nitropyridin-2-amin (7)

The synthetic method was similar to that described for 3 except that the starting material 2-chloro-3-nitropyridine (1 g, 6.33 mmol) was reacted with Trimethylaniline. Yellow solid, yield 67.1%. Melting point: 158-160° C. $^1$H NMR (400 MHz, DMSO-d₆) δ 9.53 (s, 1H, NH), 8.50 (dd, J=8.3, 1.7 Hz, 1H, Pyr-H), 8.32 (dd, J=4.4, 1.7 Hz, 1H, Pyr-H), 6.94 (s, 2H, Ph-H), 6.83 (dd, J=8.3, 4.4 Hz, 1H, Pyr-H), 2.27 (s, 3H, CH₃), 2.06 (s, 6H, 2×CH₃). $^{13}$C NMR (100 MHz, DMSO-d₆) δ 156.3, 151.6, 136.1, 135.9, 135.8, 133.9, 128.8, 128.2, 113.3, 21.0, 18.5. C₁₄H₁₅N₃O₂ (Exact Mass: 257.1164).

Step B: N²-Mesitylpyridine-2,3-diamine (8)

The synthetic method was similar to that described for 4.

White solid, yield 70.8%. Melting point: 172.5-174° C. $^1$H NMR (400 MHz, DMSO-d₆) δ 7.19 (dd, J=4.9, 1.4 Hz, 1H, Pyr-H), 6.85 (s, 2H, Ph-H), 6.81 (s, H, NH), 6.78-6.76 (m, 2H, Pyr-H), 6.40 (dd, J=7.4, 4.9 Hz, 1H), 4.90 (s, 2H, NH₂), 2.23 (s, 3H CH₃), 2.04 (s, 6H, 2×CH₃). $^{13}$C NMR (100 MHz, DMSO-d₆) δ 146.6, 136.5, 135.5, 135.1, 133.9, 130.9, 128.7, 118.6, 113.9, 20.9, 18.7. C₁₄H₁₇N3 (Exact Mass: 227.1422).

Step C: 3-Mesityl-3H-imidazo[4,5-b]pyridine-2-thiol (9)

The synthetic method was similar to that described for 5.

White solid, Yield 75.1%. Melting point: 274-280° C. $^1$H NMR (400 MHz, DMSO-d₆) δ 13.23 (s, 1H, SH), 8.07 (dd, J=5.0, 1.3 Hz, 1H, Pyr-H), 7.63 (dd, J=7.9, 1.3 Hz, 1H, Pyr-H), 7.24 (dd, J=7.9, 5.0 Hz, 1H, Pyr-H), 7.06 (s, 2H, Ph-H), 2.33 (s, 3H, CH₃), 1.85 (s, 6H, 2×CH₃). $^{13}$C NMR (100 MHz, DMSO-d₆) δ 170.0, 146.0, 143.1, 139.0, 136.6, 130.4, 129.2, 125.3, 119.5, 117.4, 21.1, 17.9.

C₁₅H₁₅N3S (Exact Mass: 269.0987).

Example 11: Preparation of X1

Synthesized in a similar procedure with example 2 using intermediate 9.

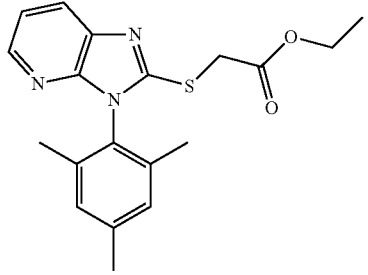

White solid, yield 67.1%, Melting point: 115-116.5° C. $^1$H NMR (400 MHz, DMSO-d₆) δ 8.15 (dd, J=4.8, 1.4 Hz, 1H, Pyr-H), 8.02 (dd, J=8.0, 1.4 Hz, 1H, Pyr-H), 7.27 (dd, J=8.0, 4.8 Hz, 1H, Pyr-H), 7.14 (s, 2H, PhH), 4.26 (s, 2H, CH₂), 4.13 (q, J=7.1 Hz, 2H, CH₂), 2.36 (s, 3H, CH₃), 1.85 (s, 6H, 2×CH₃), 1.17 (t, J=7.1 Hz, 3H, CH₃). $^{13}$C NMR (100 MHz, DMSO-d₆) δ 168.5, 153.9, 149.3, 143.3, 140.1, 136.8, 135.4, 129.7, 129.2, 125.6, 118.8, 61.7, 32.9, 21.2, 17.5, 14.4. ESI-MS: m/z 356.1429 [M+H]⁺. C₁₉H₂₁N₃O₂S (Exact Mass: 355.1354).

Example 12: Preparation of X2

Synthesized in a similar procedure with example 11 using ethyl 4-bromobutyrate as ester.

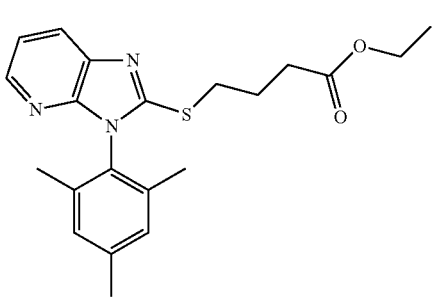

Yellow oil, yield 71.9%. $^1$H NMR (400 MHz, DMSO-d₆) δ 8.13 (dd, J=4.8, 1.4 Hz, 1H, Pyr-H), 8.03 (dd, J=8.0, 1.4 Hz, 1H, Pyr-H), 7.27 (dd, J=8.0, 4.8 Hz, 1H, Pyr-H), 7.12 (s, 2H, Ph-H), 4.04 (q, J=7.1 Hz, 2H, CH₂), 3.38-3.34 (2H, CH₂), 2.43 (t, J=7.3 Hz, 2H, CH₂), 2.35 (s, 3H, CH₃), 2.00 (p, J=7.2 Hz, 2H, CH₂), 1.81 (s, 6H, 2×CH₃), 1.15 (t, J=7.1 Hz, 3H, CH₃). $^{13}$C NMR (100 MHz, DMSO-d₆) δ 172.6, 154.5, 149.3, 143.1, 139.9, 136.7, 135.5, 129.6, 129.4, 125.4, 118.7, 60.3, 32.6, 30.1, 24.9, 21.1, 17.5, 14.5. ESI-MS: m/z 384.1744 [M+H]⁺. C₂₁H₂₅N₃O₂S (Exact Mass: 383.1667).

Example 13: Preparation of X3

Synthesized in a similar procedure with example 11 using ethyl 2-chloropropionate as ester.

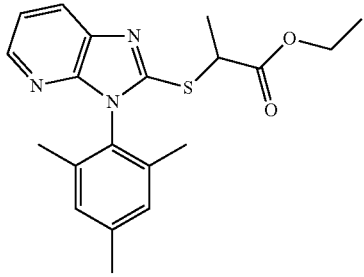

White solid, yield 68.5%. Melting point: 70-70.5° C. $^1$H NMR (400 MHz, DMSO-d$_6$) δ 8.16 (dd, J=4.8, 1.4 Hz, 1H, Pyr-H), 8.03 (dd, J=8.0, 1.4 Hz, 1H, Pyr-H), 7.28 (dd, J=8.0, 4.8 Hz, 1H, Pyr-H), 7.13 (s, 2H, Ph-H), 4.73 (q, J=7.3 Hz, 1H, CH), 4.12 (q, J=7.1 Hz, 2H, CH$_2$), 2.35 (s, 3H, CH$_3$), 1.83 (s, 6H, 2×CH$_3$), 1.60 (d, J=7.3 Hz, 3H, CH$_3$), 1.14 (t, J=7.1 Hz, 3H, CH$_3$). $^{13}$C NMR (100 MHz, DMSO-d$_6$) δ 171.3, 153.1, 149.0, 143.5, 140.1, 136.8, 136.7, 135.4, 129.8, 129.7, 129.2, 125.7, 118.9, 61.8, 43.0, 21.1, 18.1, 17.6, 17.5, 14.3. ESI-MS: m/z 370.1582 [M+H]+. C$_{20}$H$_{23}$N$_3$O$_2$S (Exact Mass: 369.1511).

Example 14: Preparation of X4

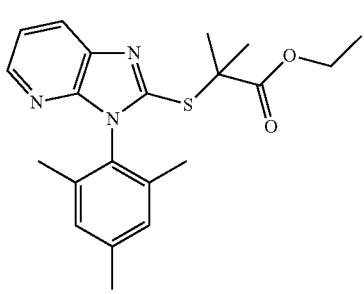 [SMILES: CCOC(=O)C(C)(C)Sc1nc2cccnc2n1-c1c(C)cc(C)cc1C]

Synthesized in a similar procedure with example 11 using ethyl 2-bromo-2-methylpropionate as ester.

White solid, yield 73.6%. Melting point: 93-95° C. $^1$H NMR (400 MHz, DMSO-d$_6$) δ 8.14 (dd, J=4.8, 1.3 Hz, 1H, Pyr-H), 7.99 (dd, J=8.0, 1.3 Hz, 1H, Pyr-H), 7.26 (dd, J=8.0, 4.8 Hz, 1H, Pyr-H), 7.12 (s, 2H, Ph-H), 4.10 (q, J=7.1 Hz, 2H, CH$_2$), 2.35 (s, 3H, CH$_3$), 1.82 (s, 6H, 2×CH$_3$), 1.73 (s, 6H, 2×CH$_3$), 1.05 (t, J=7.1 Hz, 3H, CH$_3$). $^{13}$C NMR (100 MHz, DMSO-d$_6$) δ 172.9, 152.8, 148.5, 143.4, 140.0, 136.7, 135.5, 129.6, 129.3, 125.6, 118.8, 61.7, 52.5, 26.8, 21.1, 17.5, 14.2. ESI-MS: m/z 384.1742 [M+H]+. C$_{21}$H$_{25}$N$_3$O$_2$S (383.1667).

Example 15: Preparation of X5

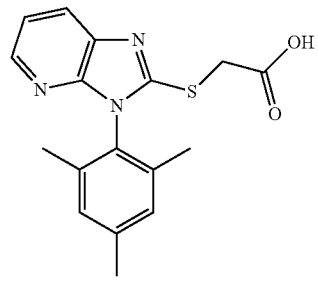 [SMILES: Cc1cc(C)c(-n2c(SCC(=O)O)nc3cccnc32)c(C)c1]

Synthesized in a similar procedure with example 6.

White solid, yield 94.2%. Melting point: 190-200.5° C. $^1$H NMR (400 MHz, DMSO-d$_6$) δ 8.14 (dd, J=4.8, 1.4 Hz, 1H, Pyr-H), 8.03 (dd, J=8.0, 1.4 Hz, 1H, Pyr-H), 7.27 (dd, J=8.0, 4.8 Hz, 1H, Pyr-H), 7.14 (s, 2H, Ph-H), 4.19 (s, 2H, CH$_2$), 2.36 (s, 3H, CH$_3$), 1.85 (s, 6H, 2×CH$_3$). $^{13}$C NMR (100 MHz, DMSO-d$_6$) δ 169.7, 154.2, 149.3, 143.2, 140.0, 136.9, 135.4, 129.6, 129.3, 125.5, 118.7, 33.4, 21.2, 17.5. ESI-MS: m/z 328.1116 [M+H]+. C$_{17}$H$_{21}$N$_3$O$_2$S (Exact Mass: 327.1041).

Example 16: Preparation of X6

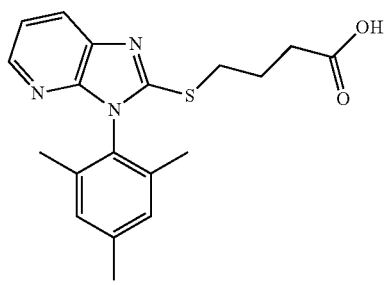 [SMILES: Cc1cc(C)c(-n2c(SCCCC(=O)O)nc3cccnc32)c(C)c1]

Synthesized in a similar procedure with example 6.

White solid, yield 90.0%. Melting point: 138-140° C. $^1$H NMR (400 MHz, DMSO-d$_6$) δ 8.13 (dd, J=4.8, 1.3 Hz, 1H, Pyr-H), 8.03 (dd, J=8.0, 1.3 Hz, 1H, Pyr-H), 7.27 (dd, J=8.0, 4.8 Hz, 1H, Pyr-H), 7.12 (s, 2H, Ph-H), 3.47-3.42 (m, 2H, CH$_2$), 2.38-2.35 (m, 5H, CH$_2$+CH$_3$), 2.01-1.94 (m, 2H, CH$_2$), 1.82 (s, 6H, 2×CH$_3$). $^{13}$C NMR (100 MHz, DMSO-d$_6$) δ 174.2, 154.6, 149.3, 143.1, 139.9, 136.7, 135.6, 129.6, 129.4, 125.4, 118.7, 32.8, 30.2, 24.9, 21.1, 17.5. ESI-MS: m/z 356.1432 [M+H]+.

C$_{19}$H$_{21}$N$_3$O$_2$S (Exact Mass: 355.1354).

Example 17: Preparation of X7

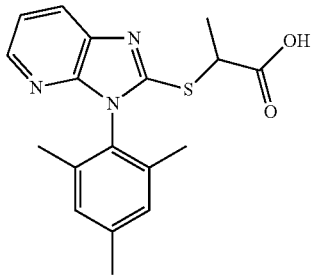 [SMILES: Cc1cc(C)c(-n2c(SC(C)C(=O)O)nc3cccnc32)c(C)c1]

X7

Synthesized in a similar procedure with example 6.

White solid, yield 93.3%. Melting point: 148-149.5° C. $^1$H NMR (400 MHz, DMSO-d$_6$) 13.14 (s, 1H, OH), 8.16 (dd, J=4.8, 1.3 Hz, 1H, Pyr-H), 8.05 (dd, J=8.0, 1.3 Hz, 1H, Pyr-H), 7.28 (dd, J=8.0, 4.8 Hz, 1H, Pyr-H), 7.13 (s, 2H, Ph-H), 4.69 (q, J=7.2 Hz, 1H, CH), 2.36 (s, 3H, CH$_3$), 1.83 (s, 6H, 2×CH$_3$), 1.61 (d, J=7.3 Hz, 3H, CH$_3$). $^{13}$C NMR (100 MHz, DMSO-d$_6$) 172.8, 153.5, 149.1, 143.4, 140.0, 136.8, 136.7, 135.5, 129.7, 129.6, 129.3, 125.7, 118.8, 43.7, 21.1, 18.6, 17.5, 17.5. ESI-MS: m/z 342.1275 [M+H]+. C$_{18}$H$_{19}$N$_3$O$_2$S (Exact Mass: 341.1198).

Example 18: Preparation of X8

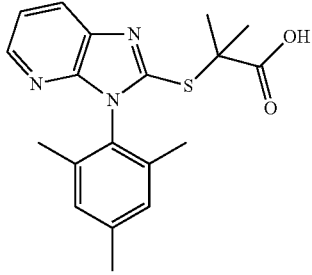 [SMILES: Cc1cc(C)c(-n2c(SC(C)(C)C(=O)O)nc3cccnc32)c(C)c1]

X8

Synthesized in a similar procedure with example 6.

White solid, yield 93.9%. Melting point: 180-183° C. $^1$H NMR (400 MHz, DMSO-d$_6$) δ 8.15 (dd, J=4.8, 1.4 Hz, 1H, Pyr-H), 8.02 (dd, J=8.0, 1.4 Hz, 1H, Pyr-H), 7.26 (dd, J=8.0, 4.8 Hz, 1H, Pyr-H), 7.11 (s, 2H, Ph-H), 2.35 (s, 3H, CH$_3$), 1.81 (s, 6H, 2×CH$_3$), 1.74 (s, 6H, 2×CH$_3$). $^{13}$C NMR (100 MHz, DMSO-d$_6$) δ 174.4, 153.1, 148.5, 143.4, 139.9, 136.7, 135.5, 129.6, 125.7, 118.7, 53.1, 26.8, 21.1, 17.5. ESI-MS: m/z 356.1428 [M+H]$^+$. C$_{19}$H$_{21}$N$_3$O$_2$S (Exact Mass: 355.1354).

Example 19: Preparation of Intermediate 20

Step A: N-(4-Cyclopropylnaphthalen-1-yl)-3-nitropyridin-2-amine (14)

The synthetic method was similar to that described for 3 except that the starting material 2-chloro-3-nitropyridine (1 g, 6.33 mmol) was reacted with 4-cyclopropyl-1-naphthylamine (11). Yellow solid, yield 68.8%. Melting point: 159-160.5. $^1$H NMR (400 MHz, DMSO-d$_6$) δ 10.16 (s, 1H, NH), 8.55 (dd, J=8.3, 1.7 Hz, 1H, Pyr-H), 8.46 (d, J=8.3 Hz, 1H, Naph-H), 8.30 (dd, J=4.4, 1.7 Hz, 1H, Pyr-H), 7.95 (d, J=8.2 Hz, 1H, Naph-H), 7.64-7.52 (m, 3H, Naph-H), 7.30 (d, J=7.6 Hz, 1H, Naph-H), 6.89 (dd, J=8.3, 4.5 Hz, 1H, Pyr-H), 2.46-2.39 (m, 1H, CH), 1.10-1.06 (m, 2H, CH$_2$), 0.77-0.74 (m, 2H, CH$_2$). $^{13}$C NMR (100 MHz, DMSO-d$_6$) δ 155.8, 151.9, 137.7, 135.8, 134.0, 133.2, 130.0, 128.9, 126.6, 126.5, 125.0, 124.0, 123.7, 123.5, 114.2, 13.3, 7.1. C$_{18}$H$_{15}$N$_3$O$_2$(Exact Mass: 305.1164).

Step B: N$^2$-(4-Cyclopropylnaphthalen-1-yl)pyridine-2,3-diamine (17)

The synthetic method was similar to that described for 4. White solid, yield 56.4%. Melting point: 171-172° C. $^1$H NMR (400 MHz, DMSO-d$_6$) δ 8.39 (d, J=8.3 Hz, 1H, Naph-H), 8.03 (d, J=8.3 Hz, 1H, Naph-H), 7.71 (s, 1H, NH), 7.56 (t, J=8.0 Hz, 1H, Naph-H), 7.47 (t, J=7.6 Hz, 1H, Naph-H), 7.41 (d, J=7.7 Hz, 1H, Naph-H), 7.31 (dd, J=4.8, 1.4 Hz, 1H, Pyr-H), 7.20 (d, J=7.7 Hz, 1H, Naph-H), 6.94 (dd, J=7.6, 1.5 Hz, 1H, Pyr-H), 6.59 (dd, J=7.5, 4.8 Hz, 1H, Pyr-H), 5.12 (s, 2H, NH$_2$), 2.37-2.30 (m, 1H, CH), 1.05-1.00 (m, 2H, CH$_2$), 0.71-0.67 (m, 2H, CH$_2$). $^{13}$C NMR (100 MHz, DMSO-d$_6$) δ 146.0, 136.6, 135.0, 134.1, 133.7, 132.5, 128.7, 126.0, 125.2, 124.8, 124.2, 123.9, 120.2, 119.0, 116.1, 13.2, 6.8. C$_{18}$H$_{17}$N$_3$(Exact Mass: 275.1422).

Step C: 3-(4-Cyclopropylnaphthalen-1-yl)-3H-imidazo[4,5-b]pyridine-2-thiol (20)

The synthetic method was similar to that described for 5. White solid, yield 86.2%. Melting point: 294-296° C. $^1$H NMR (400 MHz, DMSO-d$_6$) δ 13.36 (s, 1H, SH), 8.54 (d, J=8.5 Hz, 1H, Pyr-H), 7.99 (dd, J=5.0, 1.3 Hz, 1H, Pyr-H), 7.66 (ddd, J=16.7, 8.1, 1.2 Hz, 2H, Naph-H), 7.50-7.42 (m, 3H, Naph-H+Pyr-H), 7.26-7.23 (m, 2H, Naph-H), 2.57-2.52 (m, 1H, CH), 1.19-1.11 (m, 2H, CH2), 0.90-0.81 (m, 2H, CH2). $^{13}$C NMR (100 MHz, DMSO-d$_6$) δ 171.7, 147.6, 142.8, 141.4, 134.1, 130.3, 129.9, 128.1, 127.2, 126.9, 125.4, 125.2, 123.7, 123.3, 119.6, 117.4, 13.4, 7.5, 7.3. C$_{19}$H$_{15}$N3S (Exact Mass: 317.0987).

Example 20: Preparation of Q1

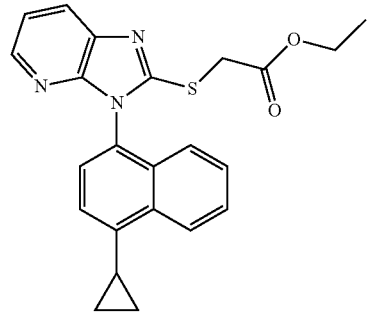 [SMILES: CCOC(=O)CSc1nc2cccnc2n1-c1ccc(C2CC2)c2ccccc12]

Q1

Synthesized in a similar procedure with example 2 using intermediate 20.

White solid, yield 67.1%. Melting point: 141-143.5° C. $^1$H NMR (400 MHz, DMSO-d$_6$) δ 8.59 (d, J=8.5 Hz, 1H, Pyr-H), 8.10 (s, 1H, Naph-H), 8.08 (d, J=1.8 Hz, 1H, Naph-H), 7.70 (t, J=8.2 Hz, 1H, Naph-H), 7.61 (d, J=7.6 Hz, 1H, Pyr-H), 7.51 (t, J=7.6 Hz, 1H, Pyr-H), 7.47 (d, J=7.5 Hz, 1H, Naph-H), 7.31-7.28 (m, 1H, Naph-H), 7.07 (d, J=8.3 Hz, 1H, Naph-H), 4.24 (d, J=2.3 Hz, 2H, CH$_2$), 4.13 (q, J=7.0 Hz, 2H, CH$_2$), 2.61-2.54 (m, 1H, CH), 1.20-1.15 (m, 5H, CH$_2$+CH$_3$), 0.93-0.82 (m, 2H, CH$_2$). $^{13}$C NMR (100 MHz, DMSO-d$_6$) δ 168.5, 154.9, 151.0, 143.3, 142.5, 135.3, 134.2, 130.0, 128.3, 127.8, 127.5, 127.3, 125.8, 125.4, 123.3, 123.1, 119.1, 61.7, 33.4, 14.4, 13.4, 7.7, 7.4. ESI-MS: m/z 404.1432 [M+H]+. C$_{23}$H$_{21}$N$_3$O$_2$S (Exact Mass: 403.1354).

Example 21: Preparation of Q2

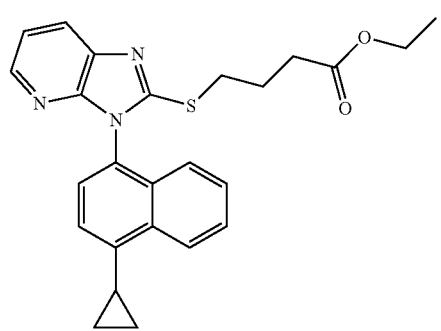

Synthesized in a similar procedure with example 20 using ethyl 4-bromobutyrate as ester.

White solid, yield 71.9%. Melting point: 79-80.5° C. $^1$H NMR (400 MHz, DMSO-d$_6$) δ 8.57 (d, J=8.5 Hz, 1H, Pyr-H), 8.11-8.06 (m, 2H, Naph-H), 7.68 (ddd, J=8.3, 6.9, 1.1 Hz, 1H, Naph-H), 7.60 (d, J=7.6 Hz, 1H, Naph-H), 7.51-7.47 (m, 1H, Pyr-H), 7.44 (d, J=7.5 Hz, 1H, Naph-H), 7.29 (dd, J=8.0, 4.9 Hz, 1H, Pyr-H), 7.03 (d, J=8.3 Hz, 1H, Naph-H), 4.02 (q, J=7.1 Hz, 2H, CH$_2$), 3.36-3.32 (m, 2H, CH$_2$), 2.59-2.54 (d, J=22.2 Hz, 1H, CH), 2.39 (t, J=7.3 Hz, 2H, CH$_2$), 2.02-1.95 (m, 2H, CH$_2$), 1.17-1.11 (m, 5H, CH$_2$+CH$_3$), 0.91-0.81 (m, 2H, CH$_2$). $^{13}$C NMR (100 MHz, DMSO-d$_6$) δ 172.6, 155.6, 151.0, 143.1, 142.3, 135.5, 134.1, 130.1, 128.6, 127.8, 127.6, 127.3, 125.5, 125.4, 123.2, 123.0, 118.9, 60.3, 40.6, 40.4, 40.1, 39.9, 39.7, 39.5, 39.3, 32.6, 30.5, 24.7, 14.5, 13.4, 7.7, 7.4. ESI-MS: m/z 432.1742 [M+H]$^+$. C$_{25}$H$_{25}$N$_3$O$_2$S (Exact Mass: 431.1667).

Example 22: Preparation of Q3

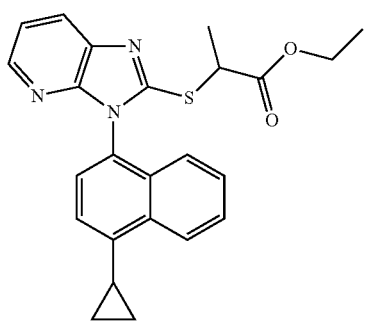

Synthesized in a similar procedure with example 20 using ethyl 2-chloropropionate as ester.

White solid, yield 68.5%. Melting point: 111.5-112° C. $^1$H NMR (400 MHz, DMSO-d$_6$) δ 8.58 (d, J=8.5 Hz, 1H, Pyr-H), 8.10 (d, J=7.1 Hz, 2H, Naph-H), 7.69 (t, J=8.2 Hz, 1H, Naph-H), 7.59 (t, J=8.2 Hz, 1H, Naph-H), 7.50 (t, J=8.3 Hz, 1H, Naph-H), 7.45 (dd, J=7.5, 3.1 Hz, 1H, Pyr-H), 7.32-7.29 (m, 1H, Pyr-H), 7.03 (t, J=7.4 Hz, 1H, Naph-H), 4.75-4.66 (m, 1H, CH), 4.18-4.06 (m, 2H, CH$_2$), 2.59-2.53 (m, 1H, CH), 1.55 (t, J=7.2 Hz, 3H, CH$_3$), 1.18-1.10 (m, 5H, CH$_2$+CH$_3$), 0.91-0.82 (m, 2H, CH$_2$). $^{13}$C NMR (100 MHz, DMSO-d$_6$) δ 171.3, 153.9, 150.7, 143.5, 142.6, 135.4, 134.1, 130.0, 128.3, 127.9, 127.6, 127.4, 125.9, 125.4, 123.2, 122.9, 119.2, 61.8, 43.5, 18.1, 14.3, 13.4, 7.7, 7.4. ESI-MS: m/z 418.1589 [M+H]+. C$_{24}$H$_{23}$N$_3$O$_2$S (Exact Mass: 417.1511).

Example 23: Preparation of Q4

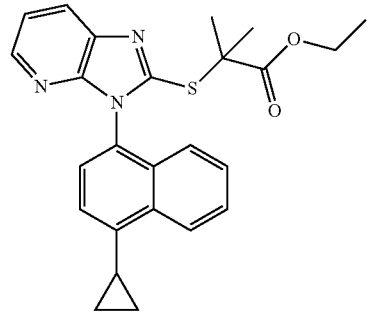 [SMILES: CCOC(=O)C(C)(C)Sc1nc2cccnc2n1-c1ccc(C2CC2)c2ccccc12]

Synthesized in a similar procedure with example 20 using ethyl 2-bromo-2-methylpropionate as ester.

white solid, yield 73.6%. Melting point: 117.5-118° C. $^1$H NMR (400 MHz, DMSO-d$_6$) δ 8.58 (d, J=8.5 Hz, 1H, Pyr-H), 8.11-8.07 (m, 2H, Naph-H), 7.71-7.67 (m, 1H, Naph-H), 7.56 (d, J=7.6 Hz, 1H, Naph-H), 7.51 (t, J=8.1 Hz, 1H, Pyr-H), 7.45 (d, J=7.6 Hz, 1H, Naph-H), 7.30 (dd, J=8.0, 4.8 Hz, 1H, Pyr-H), 6.98 (d, J=8.3 Hz, 1H, Naph-H), 4.14-4.06 (m, 2H, CH$_2$), 2.60-2.53 (m, 1H, CH), 1.70 (s, 3H, CH$_3$), 1.63 (s, 3H, CH$_3$), 1.19-1.14 (m, 2H, CH$_2$), 1.10 (t, J=7.1 Hz, 3H, CH$_3$), 0.93-0.81 (m, 2H, CH$_2$). $^{13}$C NMR (100 MHz, DMSO-d$_6$) δ 172.8, 153.3, 150.2, 143.6, 142.4, 135.4, 134.1, 130.1, 128.6, 127.8, 127.5, 127.3, 126.0, 125.4, 123.2, 122.9, 119.2, 61.7, 53.0, 26.8, 26.7, 14.3, 13.4, 7.7, 7.4. ESI-MS: m/z 432.1735 [M+H]$^+$. C$_{25}$H$_{25}$N$_3$O$_2$S (Exact Mass: 431.1667).

Example 24: Preparation of Q5

Synthesized in a similar procedure with example 6.
White solid, yield 94.2%. Melting point: 202-204° C. $^1$H NMR (400 MHz, DMSO-d$_6$) δ 12.99 (s, 1H, OH), 8.59 (d, J=8.5 Hz, 1H, Pyr-H), 8.11-8.08 (d, J=13.0 Hz, 2H, Naph- H), 7.70 (ddd, J=8.3, 6.9, 1.0 Hz, 1H, Naph-H), 7.61 (d, J=7.6 Hz, 1H, Naph-H), 7.53-7.49 (m, 1H, Pyr-H), 7.46 (d, J=7.6 Hz, 1H, Naph-H), 7.30 (dd, J=7.9, 4.9 Hz, 1H, Pyr-H), 7.07 (d, J=8.3 Hz, 1H, Naph-H), 4.18 (s, 2H, CH$_2$), 2.61-2.54 (m, 1H, CH), 1.19-1.14 (m, 2H, CH$_2$), 0.93-0.83 (d, J=42.1 Hz, 2H, CH$_2$). $^{13}$C NMR (100 MHz, DMSO-d$_6$) δ 169.7, 155.2, 151.0, 143.2, 142.5, 135.4, 134.1, 130.0, 128.4, 127.8, 127.5, 127.3, 125.7, 125.4, 123.3, 123.1, 119.0, 33.9, 13.4, 7.7, 7.4. ESI-MS: m/z 376.1110 [M+H]$^+$. C$_{21}$H$_{17}$N$_3$O$_2$S (Exact Mass: 375.1041).

Example 25: Preparation of Q6

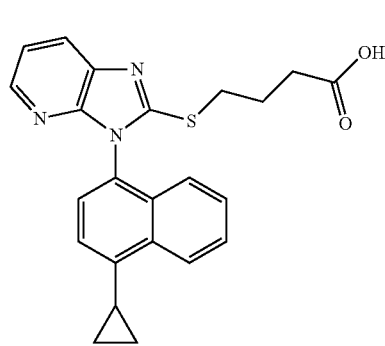 [SMILES: O=C(O)CCCSc1nc2cccnc2n1-c1ccc(C2CC2)c2ccccc12]

Q6

Synthesized in a similar procedure with example 6.

White solid, yield 90.9%. Melting point: 103-105° C. $^1$H NMR (400 MHz, DMSO-d$_6$) δ 8.57 (d, J=8.5 Hz, 1H, Pyr-H), 8.12-8.07 (m, 2H, Naph-H), 7.68 (t, J=8.1 Hz, 1H, Naph-H), 7.60 (d, J=7.6 Hz, 1H, Naph-H), 7.50 (t, J=7.9 Hz, 1H, Pyr-H), 7.44 (d, J=7.6 Hz, 1H, Naph-H), 7.30 (dd, J=8.0, 4.9 Hz, 1H, Pyr-H), 7.04 (d, J=8.4 Hz, 1H, Naph-H), 4.05-4.00 (m, 2H, CH$_2$), 2.59-2.54 (m, 1H, CH), 2.32 (t, J=7.3 Hz, 2H, CH$_2$), 1.99-1.92 (m, 2H, CH$_2$), 1.18-1.14 (m, 2H, CH$_2$), 0.91-0.81 (m, 2H, CH$_2$). $^{13}$C NMR (100 MHz, DMSO-d$_6$) δ 174.2, 155.7, 150.9, 143.1, 142.4, 135.4, 134.1, 130.1, 128.5, 127.8, 127.6, 127.3, 125.5, 125.4, 123.3, 123.0, 119.0, 32.8, 30.7, 24.7, 13.4, 7.7, 7.4. ESI-MS: m/z 404.1433 [M+H]$^+$. C$_{23}$H$_{21}$N$_3$O$_2$S (Exact Mass: 403.1354).

Example 26: Preparation of Q7

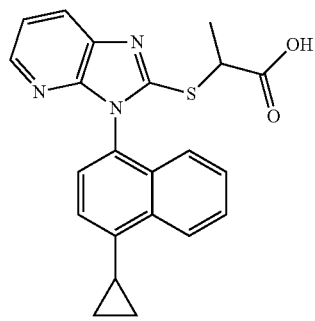

Q7

Synthesized in a similar procedure with example 6.

White solid, yield 93.3%. Melting point: 122-128° C. $^1$H NMR (400 MHz, DMSO-d$_6$) δ 13.18 (s, 1H, OH), 8.58 (d, J=8.5 Hz, 1H, Naph-H), 8.14-8.09 (m, 2H, Naph-H), 7.69 (t, J=7.7 Hz, 1H, Naph-H), 7.61 (dd, J=7.6, 4.3 Hz, 1H, Pyr-H), 7.53-7.49 (m, 1H, Naph-H), 7.46 (dd, J=7.6, 2.4 Hz, 1H, Pyr-H), 7.31 (ddd, J=8.0, 4.9, 0.6 Hz, 1H, Naph-H), 7.05 (d, J=8.4 Hz, 1H, Pyr-H), 4.69 (qd, J=7.2, 3.1 Hz, 1H, CH), 2.60-2.55 (m, 1H, CH), 1.59 (dd, J=17.5, 7.2 Hz, 3H, CH$_3$), 1.18-1.14 (m, 2H, CH$_2$), 0.92-0.83 (m, 2H, CH$_2$). $^{13}$C NMR (100 MHz, DMSO-d$_6$) δ 172.8, 154.4, 150.7, 143.4, 142.5, 135.4, 134.1, 130.0, 128.4, 127.5, 127.3, 125.8, 125.4, 123.3, 123.0, 119.1, 44.3, 18.8, 13.4, 7.7, 7.4. ESI-MS: m/z 390.1273 [M+H]$^+$. C$_{22}$H$_{19}$N$_3$O$_2$S (Exact Mass: 389.1198).

Example 27: Preparation of Q8

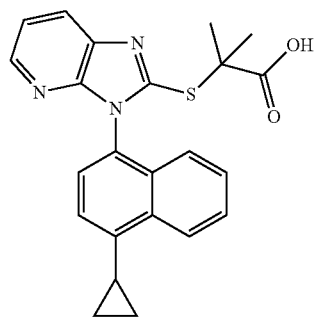 [SMILES: CC(C)(Sc1nc2cccnc2n1-c1ccc(C2CC2)c2ccccc12)C(=O)O]

Q8

Synthesized in a similar procedure with example 6.

White solid, yield 93.9%. Melting point: 171-175° C. $^1$H NMR (400 MHz, DMSO-d$_6$) δ 8.57 (d, J=8.5 Hz, 1H, Pyr-H), 8.11 (d, J=1.0 Hz, 1H, Naph-H), 8.10 (s, 1H, Naph-H), 7.68 (t, J=8.2 Hz, 1H, Pyr-H), 7.55 (d, J=7.6 Hz, 1H, Naph-H), 7.50 (t, J=7.6 Hz, 1H, Naph-H), 7.44 (d, J=7.6 Hz, 1H, Naph-H), 7.32-7.29 (m, 1H, Pyr-H), 6.99 (d, J=8.3 Hz, 1H, Naph-H), 2.59-2.53 (m, 1H, CH), 1.68 (s, 6H, 2×CH$_3$), 1.18-1.14 (m, 2H, CH$_2$), 0.93-0.81 (m, 2H, CH$_2$). $^{13}$C NMR (100 MHz, DMSO-d$_6$) δ 174.4, 153.5, 150.2, 143.6, 142.2, 135.4, 134.1, 130.2, 128.7, 127.8, 127.6, 127.2, 126.1, 125.4, 123.2, 123.0, 119.1, 53.6, 26.8, 13.4, 7.7, 7.3. ESI-MS: m/z 404.1428 [M+H]$^+$. C$_{23}$H$_{21}$N$_3$O$_2$S (Exact Mass: 403.1354).

Example 28: Preparation of Intermediate 21

Step A: N-(4-Cyclopropylnaphthalen-1-yl)-3-nitropyridin-4-amine (15)

1-naphthylamine (20.0 g, 90 mmol), cyclopropylboronic acid (10.0 g, 116 mmol), phosphoric acid (64.0 g, 300 mmol) and palladium tetrakistriphenylphosphine (7.0 g, 6 mmol) was added into a mixed solvent of 100 mL toluene and 4 mL water, and heated at 100° C. for 12 h under the protection of nitrogen. After the reaction was completed, the mixture was cooled to room temperature and 100 mL H$_2$O was added to the reaction mixture. The mixture was extracted with ethyl acetate and then dried over sodium sulfate. Filtration and concentration under reduced pressure to give 13.8 g of the crude intermediate of 4-cyclopropyl-1-naphthylamine, yield 83.6%. Chloropyridine (1 g, 6.33 mmol), 4-cyclopropyl-1-naphthylamine (1.4 g, 7.6 mmol) and sodium bicarbonate (1.6 g, 18.9 mmol) were dissolved in 50 mL ethanol solution, refluxed at 60° C. for 10 h, then the reaction mixture was cooled to room temperature and 30 mL dichloromethane was added to the residue. The mixture was washed with saturated sodium chloride (3×10 mL), and the organic layer was separated, dried over anhydrous sodium sulfate, filtered and concentrated under reduced pressure followed by flash column chromatography to give intermediate N-(4-cyclopropylnaphthalen-1-yl)-3-nitro-4-amine (15). Yellow solid, yield 69.8%. Melting point: 116-118° C. $^1$H NMR (400 MHz, DMSO-d$_6$) δ 10.06 (s, 1H, NH), 9.14 (s, 1H, Pyr-H), 8.51 (d, J=8.3 Hz, 1H, Pyr-H), 8.08 (d, J=6.1 Hz, 1H, Naph-H), 7.91 (d, J=8.1 Hz, 1H, Pyr-H), 7.69-7.65 (m, 1H, Naph-H), 7.59-7.55 (m, 1H, Naph-H), 7.45 (d, J=7.6 Hz, 1H, Naph-H), 7.36 (d, J=7.6 Hz, 1H, Naph-H), 6.29 (s, 1H, Naph-H), 2.50-2.45 (m, 1H, CH), 1.14-1.09 (m, 2H, CH$_2$), 0.81-0.77 (m, 2H, CH$_2$). $^{13}$C NMR (100 MHz, DMSO-d$_6$) δ 153.3, 148.8, 148.5, 139.8, 134.3, 132.2, 130.3, 130.1, 127.2, 127.1, 125.5, 125.3, 123.7, 123.6, 110.4, 13.3, 7.3 (2×C). ESI-MS: m/z 306.4 [M+H]$^+$. C$_{18}$H$_{15}$N$_3$O$_2$ (Exact Mass: 305.12).

Step B: N4-(4-Cyclopropylnaphthalen-1-yl)pyridine-3,4-diamine (18)

The intermediate 15 (1 g, 3.28 mmol) was dissolved in ethanol (30 mL) and palladium on carbon (0.1 g) was added to the solution. The mixture was stirred under hydrogen atmosphere at room temperature overnight. The reaction was filtered and concentrated under reduced pressure.

Recrystallized from EA as a white solid N$_4$-(4-cyclopropylnaphthalen-1-yl)pyridine-3,4-diamine (18). Yield 76.2%. Melting point: 192-193° C. $^1$H NMR (400 MHz, DMSO-d$_6$) δ 8.43 (d, J=8.2 Hz, 1H, Naph-H), 7.98 (d, J=7.9 Hz, 1H, Naph-H), 7.89 (s, 1H, NH), 7.63-7.48 (m, 4H, Naph-H), 7.25 (d, J=7.6 Hz, 1H, Pyr-H), 7.19 (d, J=7.6 Hz, 1H, Pyr-H), 6.23 (d, J=5.3 Hz, 1H, Pyr-H), 4.99 (s, 2H, NH$_2$), 2.37 (m, 1H, CH), 1.08-1.06 (dm, 2H, CH$_2$), 0.74-0.70 (m, 2H, CH$_2$). $^{13}$C NMR (100 MHz, DMSO-d$_6$) δ 139.4, 139.3, 136.4, 135.9, 135.5, 134.4, 133.1, 129.0, 126.6, 125.9, 125.1, 124.0, 120.2, 108.9, 56.5, 13.2, 7.0 (2×C). ESI-MS: m/z 276.4 [M+H]$^+$. C$_{18}$H$_{17}$N$_3$(Exact Mass: 275.14).

Step C: 1-(4-Cyclopropylnaphthalen-1-yl)-1H-imidazo[4,5-c]pyridine-2-thiol (21)

The mixture of N$_4$-(4-cyclopropylnaphthalen-1-yl) pyridine-3,4-diamine (18) (0.61 g, 2.6 mmol), potassium ethylxanthogenate (0.5 g, 3.1 mmol) and sodium bicarbonate (0.05 g, 0.6 mmol) were dissolved in 12 mL mixed solvent (ethanol/water=5:1). The reaction was refluxed for 5 h, and then cooled to room temperature. A precipitate was formed by adding 5 mL water and 2 mL 2 M sodium hydroxide solution to the reaction solution, filtered, and the pH of the filtrate was adjusted to 7 with 2M hydrochloric acid solution to give a precipitate which was filtered to afforded the 1-(4-cyclopropylnaphthalen-1-yl)-1H-imidazo[4,5-c]pyridine-2-thiol (21). White solid. Yield 79.8%. Melting point: 199.5-201° C. 1H NMR (400 MHz, DMSO-d$_6$) δ 8.89 (s, 1H, Pyr-H), 8.59 (d, J=8.5 Hz, 1H, Pyr-H), 8.42 (d, J=6.3 Hz, 1H, Naph-H), 7.71 (t, J=8.0 Hz, 1H, Naph-H), 7.63 (d, J=7.6 Hz, 1H, Naph-H), 7.54 (t, J=7.4 Hz, 1H, Naph-H), 7.48 (d, J=7.6 Hz, 1H, Naph-H), 7.42 (d, J=8.4 Hz, 1H, Pyr-H), 7.05 (d, J=6.3 Hz, 1H, Naph-H), 2.60-2.54 (m, 1H, CH), 1.18-1.15 (m, 2H, CH$_2$), 0.89-0.86 (m, 2H, CH$_2$). $^{13}$C NMR (100 MHz, DMSO-d$_6$) δ 5175.2, 145.0, 142.7, 137.5, 134.2, 130.9, 129.3, 128.5, 127.8, 127.7, 127.4, 125.5, 123.9, 123.4, 123.3, 106.4, 13.4, 7.7, 7.6. ESI-MS: m/z 318.2 [M+H]$^+$. C$_{18}$H$_{17}$N$_3$(Exact Mass: 317.10).

Example 29: Preparation of P1

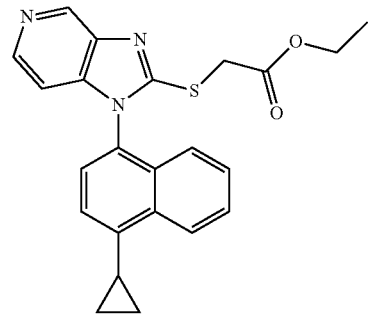 [SMILES: CCOC(=O)CSc1nc2cnccc2n1-c1ccc(C2CC2)c2ccccc12]

P1

Synthesized in a similar procedure with example 2 using intermediate 21.

White solid, yield 76.1%. Melting point: 117-120° C. $^1$H NMR (400 MHz, DMSO-d$_6$) δ 8.97 (s, 1H, Pyr-H), 8.61 (d, J=8.5 Hz, 1H, Pyr-H), 8.22 (d, J=5.5 Hz, 1H, Naph-H), 7.72 (t, J=7.7 Hz, 1H, Naph-H), 7.66 (d, J=7.6 Hz, 1H, Naph-H), 7.55 (t, J=7.6 Hz, 1H, Naph-H), 7.48 (d, J=7.6 Hz, 1H, Naph-H), 7.05 (d, J=8.2 Hz, 1H, Pyr-H), 6.90 (dd, J=5.5, 0.9 Hz, 1H, Naph-H), 4.24 (d, J=1.9 Hz, 2H, CH$_2$), 4.13 (q, J=7.0 Hz, 2H, CH$_2$), 2.62-2.55 (m, 1H, CH), 1.20-1.15 (m, 5H, CH$_2$+CH$_3$), 0.90-0.87 (m, 2H, CH$_2$). $^{13}$C NMR (100 MHz, DMSO-d$_6$) 168.4, 155.4, 143.0, 143.0, 142.6, 140.5, 140.3, 134.3, 129.4, 128.2, 128.0, 127.6, 127.1, 125.7, 123.3, 122.6, 105.6, 61.7, 34.0, 14.4, 13.4, 7.8, 7.7. ESI-MS: m/z 404.1425 [M+H]$^+$. C$_{23}$H$_{21}$N$_3$O$_2$S (Exact Mass: 403.1354).

Example 30: Preparation of P2

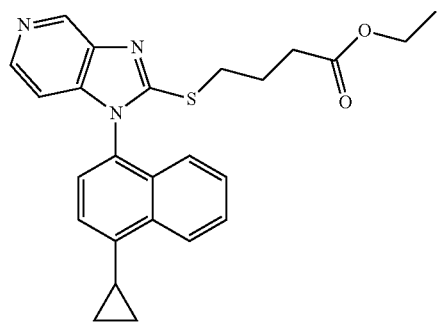 [SMILES: CCOC(=O)CCCSc1nc2cnccc2n1-c1ccc(C2CC2)c2ccccc12]

P2

Synthesized in a similar procedure with example 29 using ethyl 4-bromobutyrate as ester.

Yellow oil, yield 69.6%. $^1$H NMR (400 MHz, DMSO-d$_6$) δ 8.98 (s, 1H, Pyr-H), 8.59 (d, J=8.5 Hz, 1H, Pyr-H), 8.21 (d, J=5.5 Hz, 1H, Naph-H), 7.70 (t, J=7.7 Hz, 1H, Naph-H), 7.65 (d, J=7.6 Hz, 1H, Naph-H), 7.52 (t, J=7.7 Hz, 1H, Naph-H), 7.45 (d, J=7.6 Hz, 1H, Naph-H), 7.01 (d, J=8.3 Hz, 1H, Pyr-H), 6.86 (d, J=6.3 Hz, 1H, Naph-H), 4.02 (q, J=7.1 Hz, 2H, CH$_2$), 3.34 (t, J=7.1 Hz, 2H, CH$_2$), 2.60-2.53 (m, 1H, CH), 2.38 (t, J=7.3 Hz, 2H, CH$_2$), 1.98 (p, J=7.2 Hz, 2H, CH$_2$), 1.18-1.11 (m, 5H, CH$_2$+CH$_3$), 0.89-0.86 (m, 2H, CH$_2$). $^{13}$C NMR (100 MHz, DMSO-d$_6$) δ 172.6, 156.1, 143.0, 142.8, 142.4, 140.7, 140.1, 134.2, 129.4, 128.3, 128.1, 127.5, 127.2, 125.6, 123.3, 122.5, 105.5, 60.3, 32.5, 31.2, 24.6, 14.5, 13.4, 7.7, 7.6. ESI-MS: m/z 432.1743 [M+H]+. C25H25N3O2S (Exact Mass: 431.1667).

Example 31: Preparation of P3

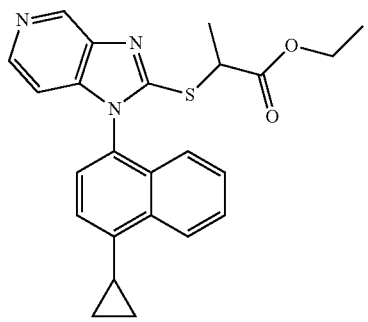 [SMILES: CCOC(=O)C(C)Sc1nc2cnccc2n1-c1ccc(C2CC2)c2ccccc12]

Synthesized in a similar procedure with example 29 using ethyl 2-chloropropionate as ester.

Yellow oil, yield 68.5%. 1H NMR (400 MHz, DMSO-d6) δ 8.99 (s, 1H, Pyr-H), 8.61 (d, J=8.5 Hz, 1H, Pyr-H), 8.23 (d, J=6.4 Hz, 1H, Naph-H), 7.72 (t, J=8.0 Hz, 1H, Pyr-H), 7.66 (t, J=7.9 Hz, 1H, Naph-H), 7.58-7.52 (m, 1H, Naph-H), 7.47 (dd, J=7.5, 2.6 Hz, 1H, Naph-H), 7.02 (t, J=7.7 Hz, 1H, Naph-H), 6.91 (ddd, J=5.5, 2.6, 0.9 Hz, 1H, Naph-H), 4.74-4.66 (m, 1H, CH), 4.17-4.07 (m, 2H, CH2), 2.61-2.55 (m, 1H, CH), 1.56 (t, J=7.2 Hz, 3H, CH3), 1.18-1.10 (m, 5H, CH2+CH3), 0.90-0.87 (m, 2H, CH2). 13C NMR (100 MHz, DMSO-d6) δ 171.2, 154.4, 143.0, 142.8, 142.6, 140.6, 140.4, 134.2, 129.4, 128.3, 128.0, 127.6, 127.1, 125.7, 123.3, 122.5, 105.7, 61.8, 44.3, 18.3, 18.1, 14.3, 13.4, 7.7. ESI-MS: m/z 418.1584 [M+H]+. C24H23N3O2S (Exact Mass: 417.1511).

Example 32: Preparation of P4

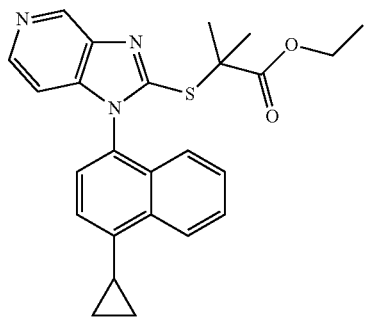 [SMILES: CCOC(=O)C(C)(C)Sc1nc2cnccc2n1-c1ccc(C2CC2)c2ccccc12]

Synthesized in a similar procedure with example 29 using ethyl 2-bromo-2-methylpropionate as ester.

White solid, yield 71.4%. Melting point: 140-142° C. 1H NMR (400 MHz, DMSO-d6) δ 8.97 (s, 1H, Pyr-H), 8.60 (d, J=8.5 Hz, 1H, Pyr-H), 8.22 (d, J=5.5 Hz, 1H, Naph-H), 7.71 (t, J=8.2 Hz, 1H, Naph-H), 7.62 (d, J=7.6 Hz, 1H, Naph-H), 7.54 (t, J=8.0 Hz, 1H, Naph-H), 7.46 (d, J=7.6 Hz, 1H, Naph-H), 6.97 (d, J=8.3 Hz, 1H, Pyr-H), 6.87 (d, J=6.3 Hz, 1H, Naph-H), 4.15-4.07 (m, 2H, CH2), 2.61-2.54 (m, 1H, CH), 1.70 (s, 3H, CH3), 1.63 (s, 3H, CH3), 1.20-1.15 (m, 2H, CH2), 1.11 (t, J=7.1 Hz, 3H, CH3), 0.90-0.86 (m, 2H, CH2). 13C NMR (100 MHz, DMSO-d6) δ 172.7, 153.5, 142.8, 142.7, 142.1, 140.7, 140.6, 134.2, 129.5, 128.3, 128.2, 127.5, 127.1, 125.6, 123.3, 122.4, 105.7, 61.7, 53.3, 26.7, 14.2, 13.4, 7.7. ESI-MS: m/z 432.1737 [M+H]+. C25H25N3O2S (Exact Mass: 431.1667).

Example 33: Preparation of P5

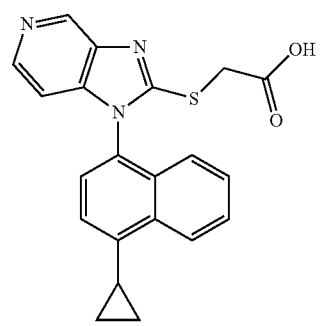 [SMILES: O=C(O)CSc1nc2cnccc2n1-c1ccc(C2CC2)c2ccccc12]

Synthesized in a similar procedure with example 6.

White solid, yield 95.1%. Melting point: 164.8-167.5° C. 1H NMR (400 MHz, DMSO-d6) δ 8.98 (s, 1H, Pyr-H), 8.61 (d, J=8.5 Hz, 1H, Pyr-H), 8.22 (d, J=5.4 Hz, 1H, Naph-H), 7.72 (t, J=7.7 Hz, 1H, Naph-H), 7.66 (d, J=7.6 Hz, 1H, Naph-H), 7.54 (t, J=7.5 Hz, 1H, Naph-H), 7.48 (d, J=7.6 Hz, 1H, Naph-H), 7.06 (d, J=8.4 Hz, 1H, Pyr-H), 6.89 (d, J=5.4 Hz, 1H, Naph-H), 4.18 (s, 2H, CH2), 2.62-2.55 (m, 1H, CH), 1.20-1.15 (m, 2H, CH2), 0.91-0.87 (m, 2H, CH2). 13C NMR (100 MHz, DMSO-d6) δ 169.6, 155.9, 143.0, 142.9, 142.4, 140.6, 140.2, 134.3, 129.4, 128.2, 128.1, 127.6, 127.1, 125.6, 123.4, 122.6, 105.5, 34.9, 13.4, 7.7, 7.6. ESI-MS: m/z 376.1118 [M+H]+. C21H17N3O2S (Exact Mass: 375.1041).

Example 34: Preparation of P6

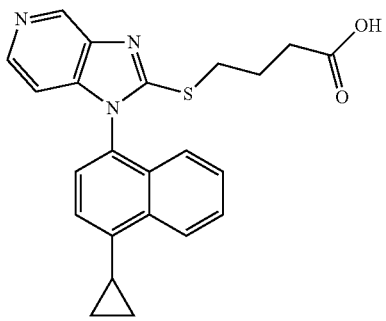 [SMILES: O=C(O)CCCSc1nc2cnccc2n1-c1ccc(C2CC2)c2ccccc12]

Synthesized in a similar procedure with example 6.

White solid, yield 94.2%. Melting point: 213-214° C. 1H NMR (400 MHz, DMSO-d6) δ 9.50 (s, 1H, Pyr-H), 8.63 (d, J=8.5 Hz, 1H, Pyr-H), 8.50 (d, J=6.5 Hz, 1H, Naph-H), 7.79 (d, J=7.6 Hz, 1H, Naph-H), 7.78-7.73 (m, 1H, Naph-H), 7.59-7.55 (m, 1H, Naph-H), 7.49 (dd, J=14.4, 7.0 Hz, 2H, Naph-H), 7.19 (d, J=8.4 Hz, 1H, Pyr-H), 3.41 (td, J=7.0, 1.8 Hz, 2H, CH2), 2.64-2.57 (m, 1H, CH), 2.34 (t, J=7.3 Hz, 2H, CH2), 2.00 (p, J=7.1 Hz, 2H, CH2), 1.21-1.17 (m, 2H, CH2), 0.92-0.88 (m, 2H, CH2). 13C NMR (100 MHz, DMSO-d6) δ

174.1, 163.0, 147.6, 143.8, 140.8, 134.9, 134.2, 132.5, 129.0, 128.5, 127.8, 127.4, 126.9, 125.7, 123.3, 122.4, 107.9, 32.7, 31.6, 24.4, 13.4, 7.9, 7.8. ESI-MS: m/z 404.1428 [M+H]$^+$. C$_{23}$H$_{21}$N$_3$O$_2$S (Exact Mass: 403.1354).

Example 35: Preparation of P7

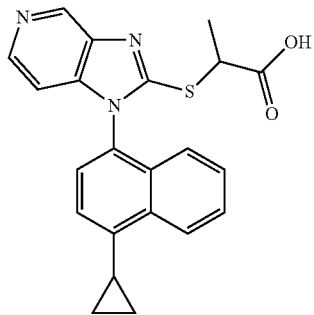 [SMILES: CC(Sc1nc2cnccc2n1-c1ccc(C2CC2)c2ccccc12)C(=O)O]

P7

Synthesized in a similar procedure with example 6.

White solid, yield 92.3%. Melting point: 160.5-163.5° C. $^1$H NMR (400 MHz, DMSO-d$_6$) δ 9.14 (s, 1H, Pyr-H), 8.62 (d, J=8.5 Hz, 1H, Pyr-H), 8.30 (d, J=5.7 Hz, 1H, Naph-H), 7.75-7.67 (m, 2H, Naph-H), 7.57-7.53 (m, 1H, Naph-H), 7.48 (d, J=7.6 Hz, 1H, Pyr-H), 7.06 (t, J=6.4 Hz, 2H, Naph-H), 4.68 (d, J=25.1 Hz, 1H, CH), 2.59 (d, J=27.6 Hz, 1H, CH), 1.60 (dd, J=16.0, 7.2 Hz, 3H, CH$_3$), 1.18 (d, J=17.7 Hz, 2H, CH$_2$), 0.89 (d, J=14.1 Hz, 2H, CH$_2$). $^{13}$C NMR (100 MHz, DMSO-d$_6$) δ 172.6, 156.5, 143.9, 143.2, 140.8, 140.6, 138.6, 134.2, 129.3, 128.3, 127.7, 127.6, 127.2, 125.7, 123.3, 122.5, 106.2, 45.1, 18.7, 13.4, 7.8, 7.6. ESI-MS: m/z 390.1276 [M+H]$^+$. C$_{22}$H$_{19}$N$_3$O$_2$S (Exact Mass: 389.1198).

Example 36: Preparation of P8

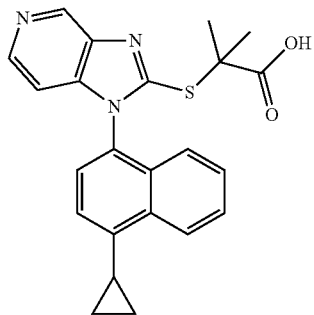 [SMILES: CC(C)(Sc1nc2cnccc2n1-c1ccc(C2CC2)c2ccccc12)C(=O)O]

P8

Synthesized in a similar procedure with example 6.

white solid, yield 94.0%. Melting point: 227-229° C. ESI-MS: m/z 404.1428 [M+H]$^+$. C$_{23}$H$_{21}$N$_3$O$_2$S (Exact Mass: 403.1354).

Example 37: Preparation of Intermediate 22

Step A: N-(4-Cyclopropylnaphthalen-1-yl)-2-nitropyridin-3-amine (16)

Palladium acetate (0.007 g, 0.0 315 mmol) and 4,5-bis(diphenylphosphino)-9,9-dimethylxanthene (0.036 g, 0.063 mmol) were dissolved in 2 mL dioxane and stirred for 15 min. A mixture of 3-chloro-2-nitropyridine (0.1 g, 0.63 mmol), 4-cyclopropyl-1-naphthylamine (0.13 g, 0.76 mmol) and cesium carbonate (0.41 g, 1.26 mmol) was dissolved in 10 mL dioxane. The two solutions were mixed and refluxed at 90° C. for 12 h under nitrogen protection. After the reaction was completed, the mixture was cooled to room temperature. After that 30 mL dichloromethane and saturated aqueous sodium chloride (3×10 mL) were added to the residue. The organic layer was separated, dried over anhydrous sodium sulfate and filtered. The product was purified by flash column chromatography to give a yellow intermediate N-(4-cyclopropylnaphthalen-1-yl)-2-nitropyridin-3-amine (16). Yellow solid, yield 60.6%. Melting point: 76-79° C. $^1$H NMR (400 MHz, DMSO-d$_6$) δ 9.45 (s, 1H, NH), 8.50 (d, J=8.4 Hz, 1H, Pyr-H), 7.95 (d, J=8.4 Hz, 1H, Pyr-H), 7.90 (d, J=5.2 Hz, 1H, Naph-H), 7.66 (t, J=7.6 Hz, 1H, Naph-H), 7.56 (t, J=8.0 Hz, 1H, Pyr-H), 7.45-7.40 (m, 2H, Naph-H), 7.34 (d, J=7.6 Hz, 1H, Naph-H), 7.00 (d, J=8.6 Hz, 1H, Naph-H), 2.48-2.43 (m, 1H, CH), 1.12-1.08 (m, 2H, CH$_2$), 0.80-0.76 (m, 2H, CH$_2$). $^{13}$C NMR (100 MHz, CDCl$_3$) δ 141.2, 140.6, 139.6, 136.9, 134.7, 131.8, 130.1, 129.9, 126.9, 126.7, 126.0, 125.3, 123.9, 123.8, 122.7, 13.3, 6.6. ESI-MS: m/z 306.4 [M+H]$^+$. C$_{18}$H$_{15}$N$_3$O$_2$ (Exact Mass: 305.12).

Step B: N$^3$-(4-Cyclopropylnaphthalen-1-yl)pyridine-2,3-diamine (19)

The synthetic method was similar to that described for 18. Yellow solid, yield 73.2%. Melting point: 143.5-144° C. $^1$H NMR (400 MHz, DMSO-d$_6$) δ 8.37 (d, J=7.8 Hz, 1H, Naph-H), 8.16 (d, J=8.2 Hz, 1H, Naph-H), 7.67 (dd, J=4.9, 1.6 Hz, 1H, Naph-H), 7.60-7.56 (m, 1H, Pyr-H), 7.53-7.49 (m, 1H, Naph-H), 7.34 (s, 1H, NH), 7.11 (d, J=7.7 Hz, 1H, Pyr-H), 6.95 (dd, J=7.6, 1.5 Hz, 1H, Naph-H), 6.62 (d, J=7.7 Hz, 1H, Pyr-H), 6.49 (dd, J=7.5, 4.9 Hz, 1H, Naph-H), 5.64 (s, 2H, NH$_2$), 2.30-2.23 (m, 1H, CH), 1.01-0.97 (m, 2H, CH$_2$), 0.65-0.61 (m, 2H, CH$_2$). $^{13}$C NMR (100 MHz, DMSO-d$_6$) δ 153.6, 141.5, 139.1, 134.4, 131.4, 127.6, 126.5, 126.3, 125.6, 125.1, 124.9, 124.4, 123.6, 113.2, 112.5, 13.1, 6.7. ESI-MS: m/z 276.1 [M+H]$^+$. C$_{18}$H$_{17}$N$_3$ (Exact Mass: 275.14).

Step C: 1-(4-Cyclopropylnaphthalen-1-yl)-1H-imidazo[4,5-b]pyridine-2-thiol (19)

N$^3$-(4-cyclopropylnaphthalen-1-yl)pyridine-2,3-diamine (19) (0.1 g, 0.36 mmol), 1,1'-thiocarbonyldiimidazole (0.1 g, 0.58 mmol) and triethylamine (0.08 mL) were dissolved in 30 mL tetrahydrofuran and refluxed at 60° C. for 5 h. After the reaction was completed, the mixture was cooled to room temperature and the solvent was evaporated under reduced pressure. The residue was washed with 30 mL dichloromethane and saturated aqueous sodium chloride (3×10 mL), and the organic layer was separated, dried over anhydrous sodium sulfate and filtered. The concentrated product was purified by flash column chromatography to give the crude intermediate 1-(4-cyclopropylnaphthalen-1-yl)-1H-imidazo[4,5-b]pyridine-2-thiol (19) as yellow solid, yield 70.9%. Melting point: 246-247° C. $^1$H NMR (400 MHz, DMSO-d$_6$) δ 13.71 (s, 1H, SH), 8.56 (d, J=8.5 Hz, 1H, Naph-H), 8.21 (dd, J=5.0, 1.3 Hz, 1H, Pyr-H), 7.69-7.65 (m, 1H, Naph-H), 7.56 (d, J=7.6 Hz, 1H, Naph-H), 7.52-7.48 (m, 1H, Naph-H), 7.44 (d, J=7.6 Hz, 1H, Naph-H), 7.27 (d, J=8.3 Hz, 1H, Naph-H), 7.07 (dd, J=7.9, 5.0 Hz, 1H, Pyr-H), 6.91 (dd, J=7.9, 1.3 Hz, 1H, Pyr-H), 2.57-2.53 (m, 1H, CH), 1.19-1.11

(m, 2H, CH$_2$), 0.89-0.82 (m, 2H, CH$_2$). $^{13}$C NMR (100 MHz, DMSO-d$_6$) δ 172.0, 146.0, 143.6, 141.7, 134.3, 129.8, 129.7, 128.5, 127.7, 127.5, 127.1, 125.4, 123.4, 123.4, 118.8, 116.7, 13.4, 7.6, 7.4. ESI-MS: m/z 318.4 [M+H]$^+$. C$_{18}$H$_{17}$N$_3$(Exact Mass: 317.10).

Example 38: Preparation of T1

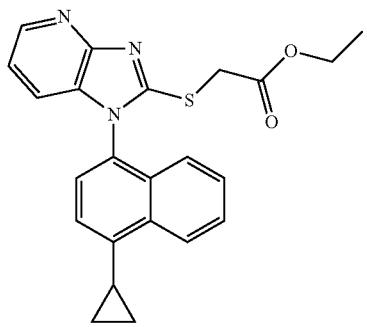 [SMILES: CCOC(=O)CSc1nc2ncccc2n1-c1ccc(C2CC2)c2ccccc12]

T1

Synthesized in a similar procedure with example 2 using intermediate 22.

Yellow oil, yield 77.6%. $^1$H NMR (400 MHz, DMSO-d$_6$) δ 8.61 (d, J=8.5 Hz, 1H, Naph-H), 8.40 (dd, J=4.8, 1.5 Hz, 1H, Pyr-H), 7.72 (ddd, J=8.3, 6.9, 1.1 Hz, 1H, Naph-H), 7.67 (d, J=7.6 Hz, 1H, Naph-H), 7.55 (t, J=8.1 Hz, 1H, Naph-H), 7.47 (d, J=7.6 Hz, 1H, Naph-H), 7.26 (dd, J=8.0, 1.5 Hz, 1H, Pyr-H), 7.13 (dd, J=8.0, 4.8 Hz, 1H, Pyr-H), 7.09 (d, J=8.2 Hz, 1H, Naph-H), 4.14 (q, J=7.1 Hz, 2H, CH$_2$), 2.62-2.55 (m, 1H, CH), 1.20 (d, J=7.1 Hz, 3H, CH$_3$), 1.06 (t, J=7.0 Hz, 4H, 2×CH$_2$), 0.91-0.87 (m, 2H, CH$_2$). $^{13}$C NMR (100 MHz, DMSO-d$_6$) δ 168.5, 156.6, 155.7, 144.2, 142.9, 134.3, 131.0, 129.5, 128.3, 128.1, 127.6, 127.2, 125.6, 123.4, 122.7, 118.4, 117.7, 61.7, 19.0, 14.4, 13.4, 7.7, 7.6. ESI-MS: m/z 404.1425 [M+H]$^+$. C$_{23}$H$_{21}$N$_3$O$_2$S (Exact Mass: 403.1354).

Example 39: Preparation of T2

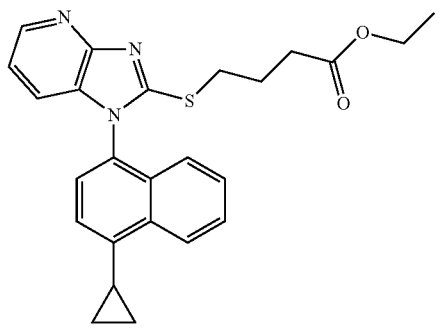 [SMILES: CCOC(=O)CCCSc1nc2ncccc2n1-c1ccc(C2CC2)c2ccccc12]

T2

Synthesized in a similar procedure with example 38 using ethyl 4-bromobutyrate as ester.

Yellow oil, yield 71.1%. $^1$H NMR (400 MHz, DMSO-d$_6$) δ 8.59 (d, J=8.5 Hz, 1H, Pyr-H), 8.40 (dd, J=4.8, 1.5 Hz, Pyr-H), 7.71 (ddd, J=9.6, 5.7, 2.3 Hz, 1H, Naph-H), 7.65 (t, J=6.4 Hz, 1H, Naph-H), 7.52 (ddd, J=8.1, 5.2, 1.0 Hz, 1H, Naph-H), 7.45 (d, J=7.6 Hz, 1H, Naph-H), 7.22 (dd, J=8.0, 1.5 Hz, 1H, Pyr-H), 7.14-7.09 (m, 1H, Naph-H), 7.05 (d, J=8.1 Hz, 1H, Naph-H), 4.03 (q, J=7.1 Hz, 2H, CH$_2$), 2.62-2.53 (m, 1H, CH), 2.44-2.36 (m, 2H, CH$_2$), 2.05-1.95 (m, 2H, CH$_2$), 1.21-1.11 (m, 5H, CH$_2$+CH$_3$), 1.07 (t, J=7.0 Hz, 2H, CH$_2$), 0.92-0.82 (m, 2H, CH$_2$). $^{13}$C NMR (100 MHz, DMSO-d$_6$) δ 172.6, 157.4, 156.0, 144.1, 142.6, 134.2, 131.0, 129.6, 128.6, 128.1, 127.5, 127.3, 125.6, 123.3, 122.6, 118.2, 117.5, 60.3, 32.6, 31.2, 24.8, 19.0, 14.5, 7.7, 7.6. ESI-MS: m/z 432.1736 [M+H]$^+$. C$_{25}$H$_{25}$N$_3$O$_2$S (Exact Mass: 431.1667).

Example 40: Preparation of T3

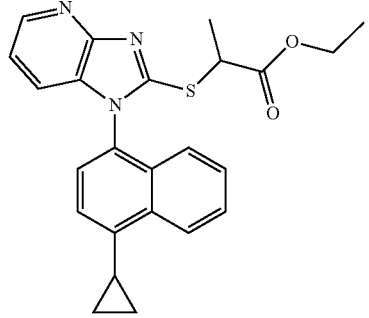 [SMILES: CCOC(=O)C(C)Sc1nc2ncccc2n1-c1ccc(C2CC2)c2ccccc12]

T3

Synthesized in a similar procedure with example 38 using ethyl 2-chloropropionate as ester.

Yellow oil, yield 69.4%. $^1$H NMR (400 MHz, DMSO-d$_6$) δ 8.60 (d, J=8.5 Hz, 1H, Pyr-H), 8.42 (dd, J=4.8, 0.8 Hz, 1H, Pyr-H), 7.75-7.68 (m, 1H, Naph-H), 7.66 (t, J=8.0 Hz, 1H, Naph-H), 7.58-7.50 (m, 1H, Naph-H), 7.46 (dd, J=7.4, 2.8 Hz, 1H, Naph-H), 7.27 (ddd, J=8.0, 2.5, 1.5 Hz, 1H, Naph-H), 7.14 (ddd, J=8.0, 4.8, 1.3 Hz, 1H, Pyr-H), 7.05 (dd, J=8.1, 5.4 Hz, 1H, Naph-H), 4.77-4.69 (m, 1H, CH), 4.16-4.07 (m, 2H, CH$_2$), 2.61-2.54 (m, 1H, CH), 1.60-1.56 (m, 3H, CH$_3$), 1.19-1.12 (m, 5H, CH$_2$+CH$_3$), 0.90-0.87 (m, 2H, CH$_2$). $^{13}$C NMR (100 MHz, DMSO-d$_6$) δ 171.2, 155.7, 144.4, 142.9, 134.2, 130.8, 129.5, 128.3, 128.2, 128.1, 127.6, 127.3, 125.6, 123.4, 122.6, 118.5, 117.9, 61.8, 18.4, 18.2, 14.3, 13.4, 7.7, 7.6. ESI-MS: m/z 418.1583 [M+H]$^+$. C$_{24}$H$_{23}$N$_3$O$_2$S (Exact Mass: 417.1511).

Example 41: Preparation of T4

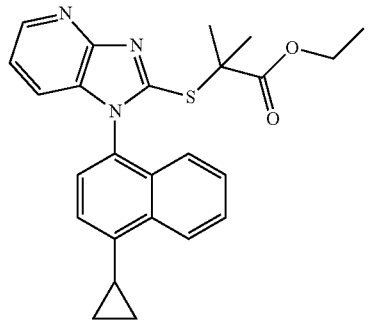 [SMILES: CCOC(=O)C(C)(C)Sc1nc2ncccc2n1-c1ccc(C2CC2)c2ccccc12]

T4

Synthesized in a similar procedure with example 38 using ethyl 2-bromo-2-methylpropionate as ester.

Yellow oil, yield 74.8%. $^1$H NMR (400 MHz, DMSO-d$_6$) δ 8.60 (d, J=8.5 Hz, 1H, Naph-H), 8.41 (dd, J=4.7, 1.5 Hz, 1H, Pyr-H), 7.72-7.68 (m, 1H, Naph-H), 7.62 (d, J=7.6 Hz, 1H, Naph-H), 7.55-7.51 (m, 1H, Naph-H), 7.45 (d, J=7.5 Hz, 1H, Naph-H), 7.23 (dd, J=8.0, 1.5 Hz, 1H, Pyr-H), 7.12 (dd, J=8.0, 4.8 Hz, 1H, Pyr-H), 7.00 (d, J=8.3 Hz, 1H, Naph-H), 4.16-4.08 (m, 2H, CH$_2$), 2.60-2.53 (m, 1H, CH), 1.71 (s, 3H, CH$_3$), 1.65 (s, 3H, CH$_3$), 1.20-1.15 (m, 2H, CH$_2$), 1.12 (t, J=7.1 Hz, 3H, CH$_3$), 0.90-0.86 (m, 2H, CH$_2$). $^{13}$C NMR (100 MHz, DMSO-d$_6$) δ 172.7, 155.8, 154.8, 144.4, 142.7, 134.2, 130.2, 129.6, 128.5, 128.1, 127.5, 127.2, 125.6, 123.3, 122.5, 118.5, 117.9, 61.7, 53.3, 26.7, 14.3, 13.4, 7.7, 7.6. ESI-MS: m/z 432.1737 [M+H]$^+$. C$_{25}$H$_{25}$N$_3$O$_2$S (Exact Mass: 431.1667).

Example 42: Preparation of T$_5$

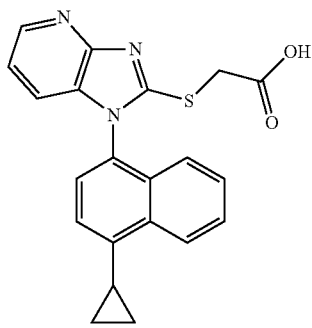 [SMILES: O=C(O)CSc1nc2ncccc2n1-c1ccc(C2CC2)c2ccccc12]

T5

Synthesized in a similar procedure with example 6.

White solid, yield 93.3%. Melting point: 151.5-153° C. $^1$H NMR (400 MHz, DMSO-d$_6$) δ 8.60 (d, J=8.5 Hz, 1H, Pyr-H), 8.38 (dd, J=4.8, 1.4 Hz, 1H, Pyr-H), 7.73-7.69 (m, 1H, Naph-H), 7.65 (d, J=7.6 Hz, 1H, Naph-H), 7.53 (t, J=7.6 Hz, 1H, Naph-H), 7.47 (d, J=7.6 Hz, 1H, Naph-H), 7.23 (dd, J=8.0, 1.4 Hz, 1H, Pyr-H), 7.12-7.07 (m, 2H, Naph-H), 4.13 (s, 2H, CH$_2$), 2.61-2.54 (m, 1H, CH), 1.19-1.14 (m, 2H, CH$_2$), 0.90-0.87 (m, 2H, CH$_2$). $^{13}$C NMR (100 MHz, DMSO-d$_6$) δ 169.6, 157.6, 155.9, 144.0, 142.7, 134.3, 130.9, 129.6, 128.6, 128.1, 127.5, 127.2, 125.6, 123.4, 122.8, 118.1, 117.5, 36.3, 13.4, 7.7, 7.5. ESI-MS: m/z 376.1114 [M+H]$^+$. C$_{21}$H$_{17}$N$_3$O$_2$S (Exact Mass: 375.1041).

Example 43: Preparation of T6

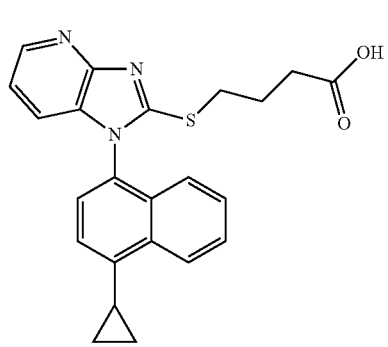 [SMILES: O=C(O)CCCSc1nc2ncccc2n1-c1ccc(C2CC2)c2ccccc12]

T6

Synthesized in a similar procedure with example 6.

White solid, yield 94.5%. Melting point: 94-97° C. $^1$H NMR (400 MHz, DMSO-d$_6$) δ 8.58 (d, J=8.5 Hz, 1H, Naph-H), 8.38 (dd, J=4.7, 1.3 Hz, 1H, Pyr-H), 7.69 (t, J=7.5 Hz, 1H, Naph-H), 7.64 (d, J=7.6 Hz, 1H, Naph-H), 7.51 (t, J=7.5 Hz, 1H, Naph-H), 7.44 (d, J=7.6 Hz, 1H, Naph-H), 7.20 (dd, J=7.9, 1.3 Hz, 1H, Pyr-H), 7.10 (dd, J=7.9, 4.8 Hz, 1H, Pyr-H), 7.04 (d, J=8.3 Hz, 1H, Naph-H), 4.08 (s, 2H, CH$_2$), 2.59-2.54 (m, 1H, CH), 2.20 (t, J=7.2 Hz, 2H, CH$_2$), 1.95-1.88 (m, 2H, CH$_2$), 1.18-1.13 (m, 2H, CH$_2$), 0.88-0.85 (m, 2H, CH$_2$). $^{13}$C NMR (100 MHz, DMSO-d$_6$) δ 157.63, 156.06, 144.09, 142.64, 134.26, 130.97, 129.6, 128.6, 128.1, 127.5, 127.2, 125.6, 123.4, 122.6, 118.1, 117.4, 34.4, 31.6, 25.38, 13.4, 7.7, 7.6. ESI-MS: m/z 404.1427 [M+H]$^+$. C$_{23}$H$_{21}$N$_3$O$_2$S (Exact Mass: 403.1354).

Example 44: Preparation of T7

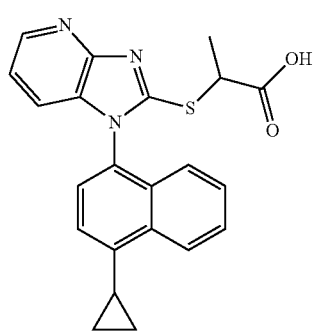 [SMILES: CC(Sc1nc2ncccc2n1-c1ccc(C2CC2)c2ccccc12)C(=O)O]

T7

Synthesized in a similar procedure with example 6.

White solid, yield 93.9%. Melting point: 156-158° C. $^1$H NMR (400 MHz, DMSO-d$_6$) δ 8.60 (d, J=8.5 Hz, 1H, Naph-H), 8.39 (d, J=4.5 Hz, 1H, Pyr-H), 7.70 (t, J=7.7 Hz, 1H, Naph-H), 7.64 (d, J=7.6 Hz, 1H, Naph-H), 7.55-7.50 (m, 1H, Naph-H), 7.46 (d, J=7.6 Hz, 1H, Naph-H), 7.22 (dd, J=7.9, 1.4 Hz, 1H, Pyr-H), 7.11 (dd, J=7.9, 4.8 Hz, 1H, Pyr-H), 7.04 (dd, J=8.2, 4.4 Hz, 1H, Naph-H), 4.59-4.54 (m, 1H, CH), 2.60-2.54 (m, 1H, CH), 1.64-1.57 (m, 3H, CH$_3$), 1.16 (d, J=8.8 Hz, 2H, CH$_2$), 0.88 (s, 2H, CH$_2$). $^{13}$C NMR (100 MHz, DMSO-d$_6$) δ 172.9, 157.4, 156.0, 144.1, 142.6, 134.2, 130.6, 129.6, 128.6, 128.1, 127.5, 127.3, 125.6, 123.4, 122.6, 118.1, 117.5, 47.4, 19.8, 13.4, 7.7, 7.5. ESI-MS: m/z 390.1275 [M+H]$^+$. C$_{22}$H$_{19}$N$_3$O$_2$S (Exact Mass: 389.1198).

Example 45: Preparation of T8

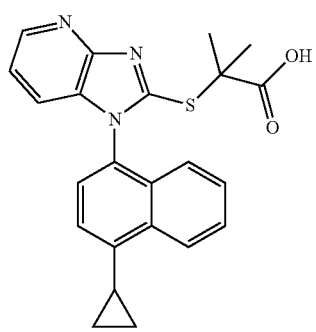 [SMILES: CC(C)(Sc1nc2ncccc2n1-c1ccc(C2CC2)c2ccccc12)C(=O)O]

T8

Synthesized in a similar procedure with example 6.

White solid, yield 90.9%. Melting point: 160-165° C. $^1$H NMR (400 MHz, DMSO-d$_6$) δ 8.59 (d, J=8.5 Hz, 1H, Naph-H), 8.42 (dd, J=4.7, 1.4 Hz, 1H, Pyr-H), 7.71 (t, J=7.6 Hz, 1H, Naph-H), 7.62 (d, J=7.6 Hz, 1H, Naph-H), 7.53 (t, J=7.6 Hz, 1H, Naph-H), 7.45 (d, J=7.6 Hz, 1H, Naph-H), 7.23 (dd, J=8.0, 1.4 Hz, 1H, Pyr-H), 7.13 (dd, J=8.0, 4.8 Hz, 1H, Pyr-H), 7.00 (d, J=8.4 Hz, 1H, Naph-H), 2.60-2.54 (m, 1H, CH), 1.70 (s, 6H, 2×CH$_3$), 1.17 (dd, J=8.4, 1.8 Hz, 2H, CH$_2$), 0.88 (q, J=5.6 Hz, 2H, CH$_2$). $^{13}$C NMR (100 MHz, DMSO-d$_6$) δ 174.3, 155.8, 155.1, 144.4, 142.6, 134.2, 130.1, 129.7, 128.6, 128.1, 127.5, 127.3, 125.6, 123.3, 122.5, 118.5, 117.9, 53.9, 26.7, 13.4, 7.7, 7.6. ESI-MS: m/z 404.1424 [M+H]$^+$. C$_{23}$H$_{21}$N$_3$O$_2$S (Exact Mass: 403.1354).

Example 46. In Vivo Activity of Reducing Serum Uric Acid

1. Materials and Method
(1) Experimental animal: Kunming mice, provided by Experimental Animal Center of Shandong University
(2) Preparation of compounds: Compounds were dissolved in ethanol and CMC-Na.
(3) Modeling drugs: Xanthine and potassium oxonate
(4) Reference drugs: Benzbromarone and Lesinurad
(5) Test method: The model group consisted of mice with acute hyperuricemia induced with 0.2 mL xanthine intragastric injection and 0.2 mL potassium oxonate subcutaneous injection, and not treated with test compound.

TABLE 2

Structures of compounds and blood uric acid concentrations

| Compounds | BUA (µM) | Compounds | BUA (µM) |
|---|---|---|---|
| M1 | 1507.6 ± 229.2 | T1 | 353.5 ± 35.6 |
| M2 | 634.7 ± 97.7 | T2 | 334 ± 65.7 |
| M3 | 1321.5 ± 183.5 | T3 | 339 ± 29.8 |
| M4 | 1363 ± 184.7 | T4 | 306 ± 46.8 |
| M5 | 1307.5 ± 195.3 | T5 | 342 ± 44.1 |
| M6 | 1342 ± 144.3 | T6 | 330 ± 29.1 |
| M7 | 1307.2 ± 133.1 | T7 | 189.7 ± 67.8 |
| M8 | 1229 ± 150.2 | T8 | 295.2 ± 54 |
| X1 | 1255.2 ± 184 | Model | 576.5 ± 120.5 |
| X2 | 1107.7 ± 195.1 | Blank | 262 ± 43.6 |
| X3 | 983.2 ± 122.6 | Blank (CMC-Na) | 286 ± 90.9 |
| X4 | 689.2 ± 53.4 | RDEA594 | 409.5 ± 124.3 |
| X5 | 1310.2 ± 155.8 | | |
| X6 | 655.2 ± 210.8 | | |
| X7 | 727.2 ± 150.7 | | |
| X8 | 1288 ± 211.5 | | |
| Q1 | 1344.75 ± 287.5 | | |
| Q2 | 1422.6 ± 194.4 | | |
| Q3 | 672 ± 76.2 | | |
| Q4 | 1328.2 ± 163.8 | | |
| Q5 | 824 ± 109.9 | | |
| Q6 | 1490.7 ± 269.9 | | |
| Q7 | 763.2 ± 248.7 | | |
| Q8 | 1448 ± 216.7 | | |
| Model | 1462.6 ± 194.3 | | |
| Blank | 377.2 ± 27.6 | | |
| Benzbromarone | 762.5 ± 30.3 | | |

2. Conclusion

It can be seen from Table 2 that in the batch 1, the compounds M2, X4, X6, X7 and Q3 all showed significant anti-gout activity, and the results were better than or equivalent to the positive control drug benzbromarone; In batch 2, the activity of T1-T8 were much better than that of drug RDEA594. It can be further developed as lead compounds.

What is claimed is:
1. A compound of imidazopyridine thioglycolic acid derivatives thereof, with formula I or II or III.

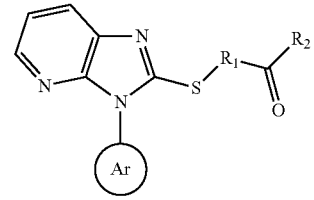

I

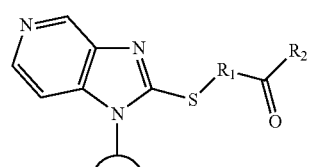

II

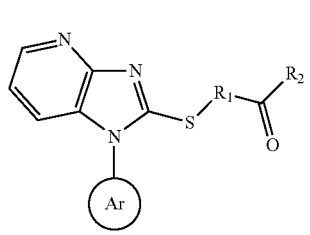

III wherein

R$_1$ is —CH$_2$—, —*CH$_2$(CH$_3$)—, —CH(CH$_3$)$_2$— or —CH$_2$CH$_2$CH$_2$—;

R2 is —OH or —OCH$_2$CH$_3$;

Ar is an optionally substituted 1-naphthyl, 2,4,6-trimethylphenyl, 4-cyclopropyl-1-naphthyl or 2-naphthyl.

2. The compound of claim 1, wherein the compound is one selected from the group consisting of formula M1, M2, M3, M4, M5, M6, M7, M8, X1, X2, X3, X4, X5, X6, X7, X8, Q1, Q2, Q3, Q4, Q5, Q6, Q7, Q8, P1, P2, P3, P4, P5, P6, P7, P8, T1, T2, T3, T4, T5, T6, T7 and T8 which are shown as following:

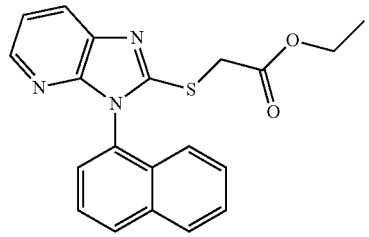

M1

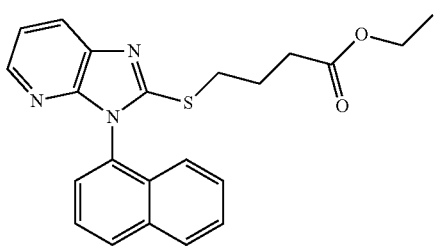

M2

M3
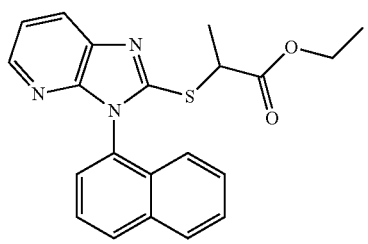
M4
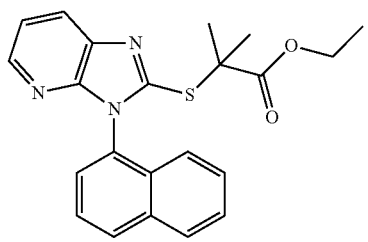
M5
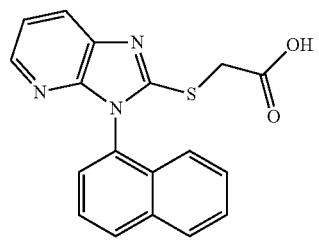
M6
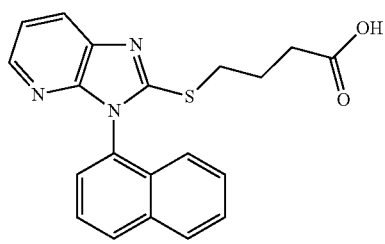
M7
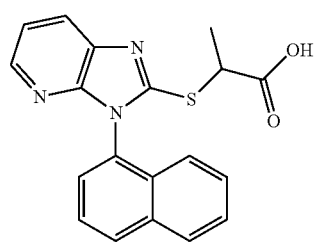
M8
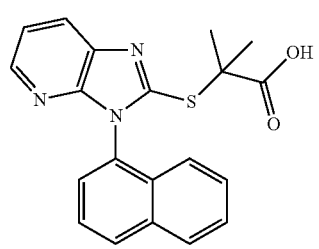
X1
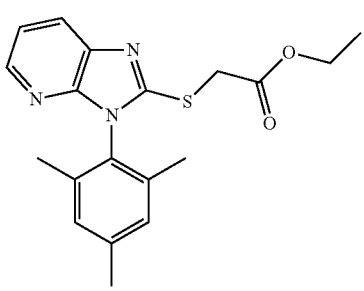
X2
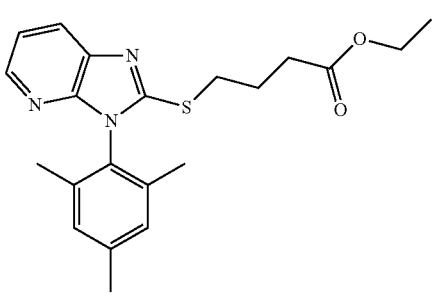
X3
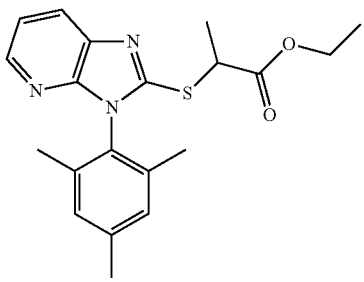
X4
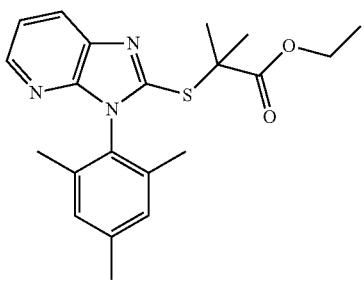
X5
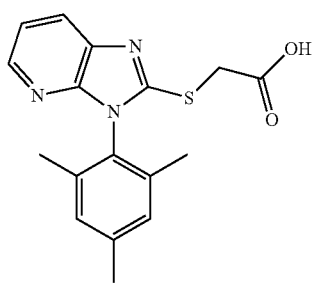

| | |
|---|---|
| 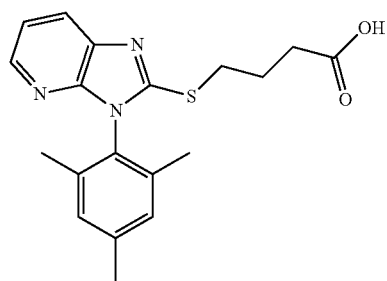 X6 | 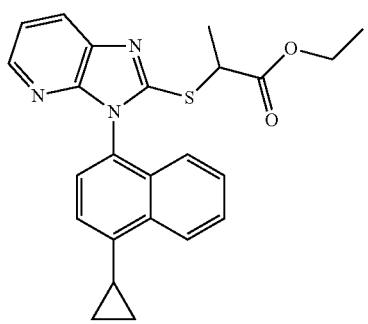 Q3 |
| 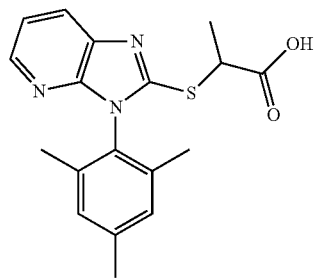 X7 | 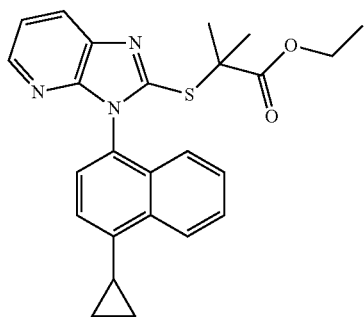 Q4 |
| 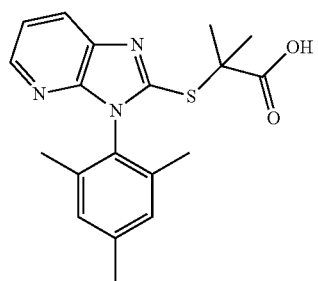 X8 | 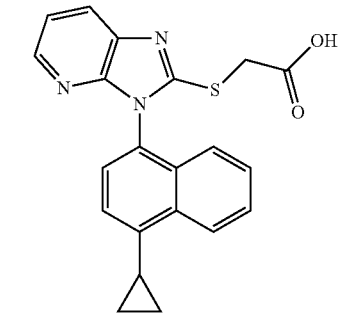 Q5 |
| 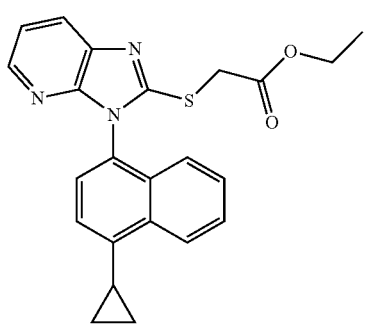 Q1 | 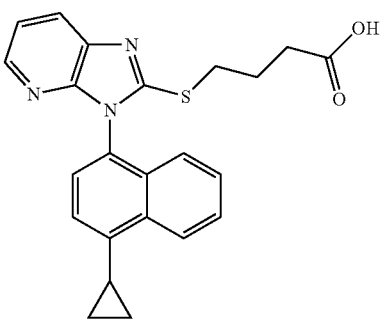 Q6 |
| 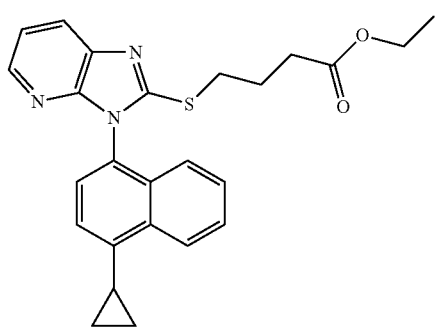 Q2 | 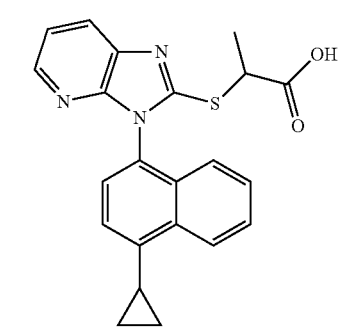 Q7 |

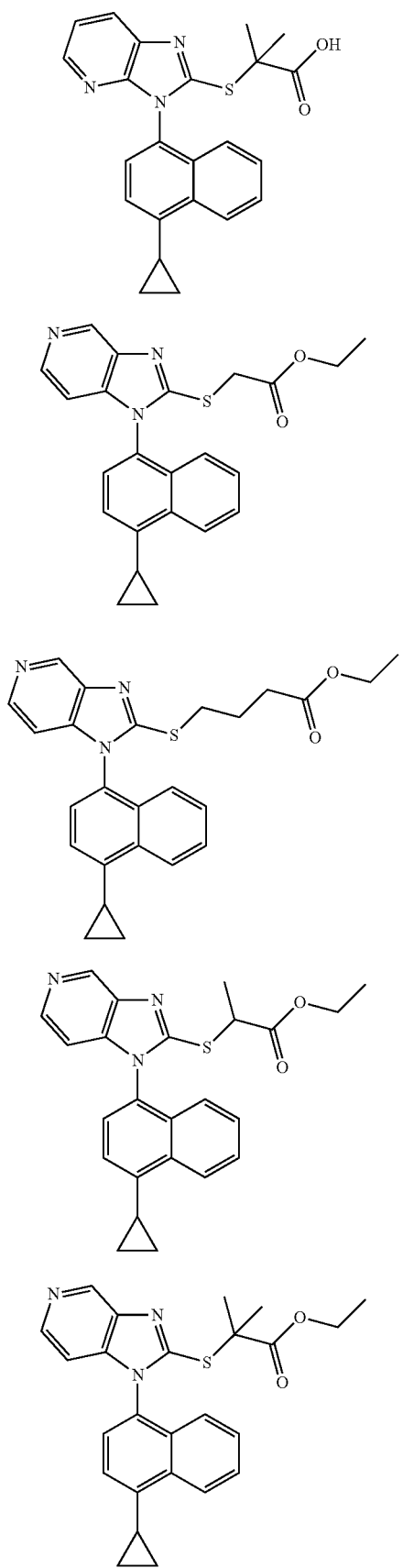
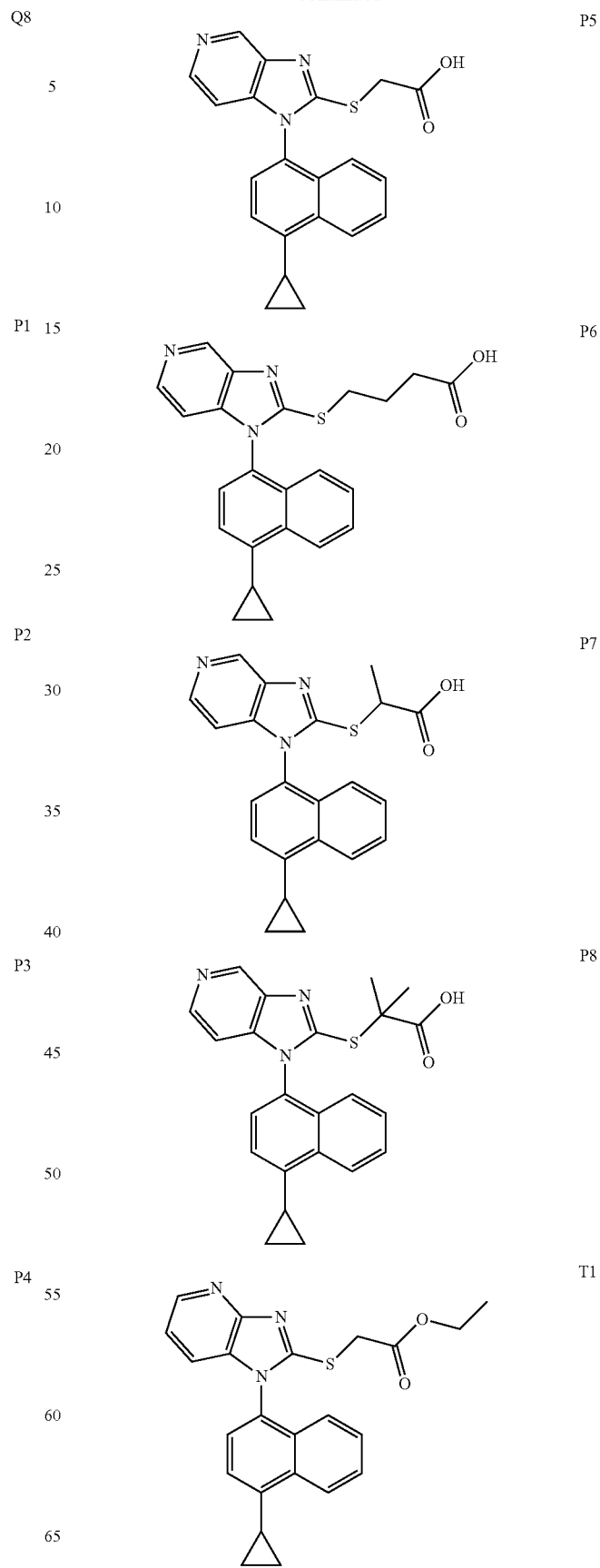

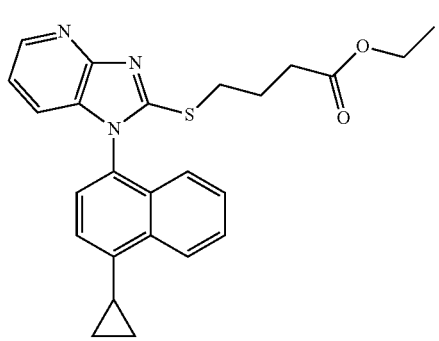

T2

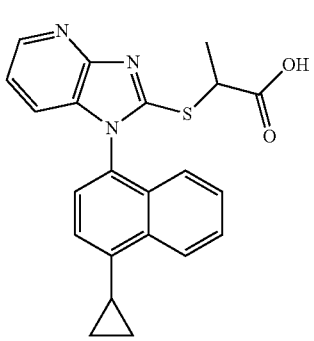

T7

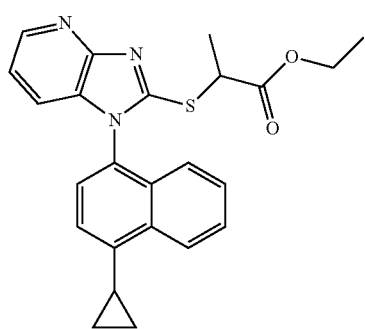

T3

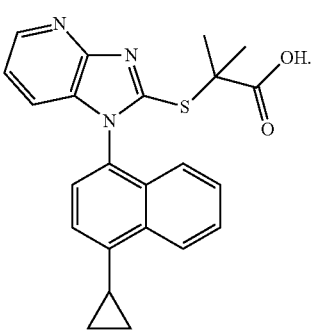

T8

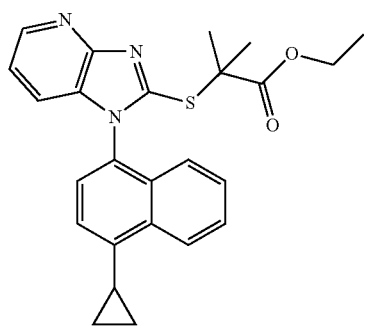

T4

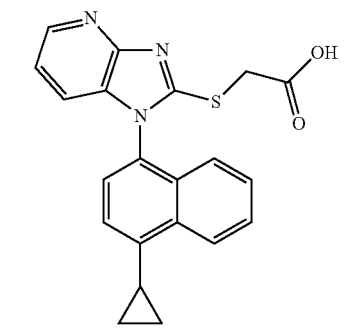

T5

3. The compound of claim 1, wherein the formula I of claim 1 is prepared as following: 3H-imidazole[4,5-b]pyridine derivatives were synthesized by well-established methods from commercially available 2-chloro-3-nitropyridine (a1), treatment of a1 with naphthalen-1-amine afforded the intermediate a2, the nitro group of a2 was reduced using Pd/C to form a3, followed by cyclization with potassium ethylxanthate and sodium bicarbonate to afford a4, nucleophilic substitution reactions of a4 afforded M1-M4, and hydrolysis with lithium hydroxide gave M5-M8, compounds X1-X8 and Q1-Q8 were similarly prepared from M1-M8, except that 2,4,6-trimethylaniline and 4-cyclopropylnaphthalen-1-amine were used, respectively;

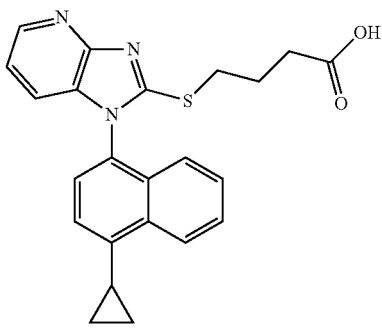

T6 scheme 1. Synthetic route to 3H-imidazole[4,5-b]pyridine derivatives

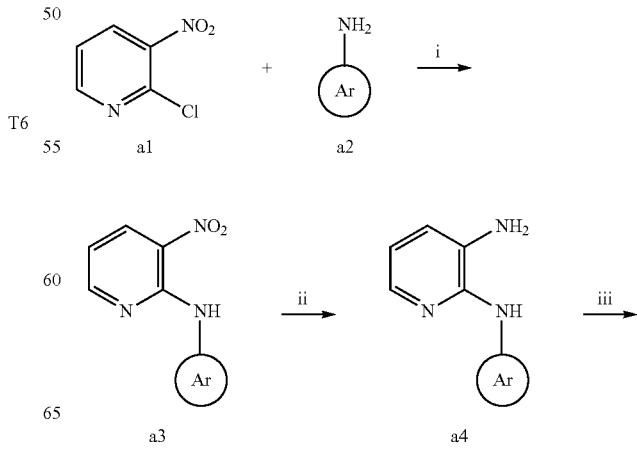

-continued

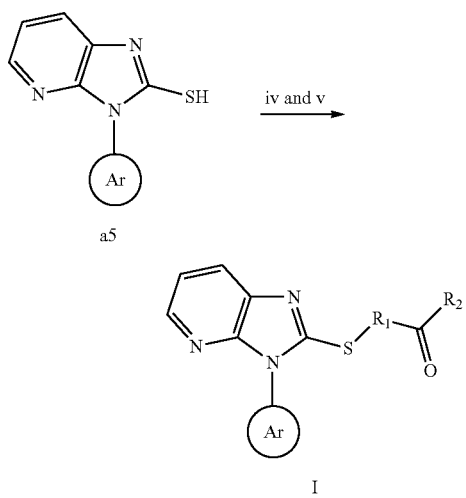

a5 iv and v

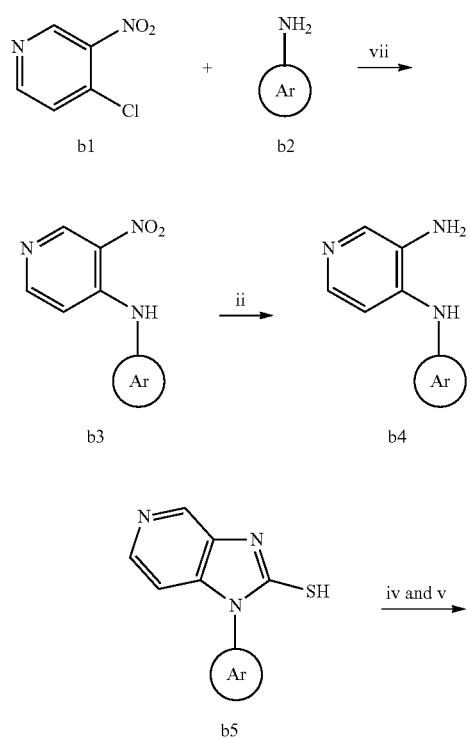

I (i) KF, 120° C.; (ii) Pd/C, H₂, EtOH; (iii) EtOCS₂K, NaHCO₃, H₂O, EtOH; (iv) ester, K₂CO₃, DMF; (v) LiOH, THF, EtOH;

wherein, the ester is selected from ethyl 4-bromobutyrate, ethyl 2-chloropropionate or ethyl 2-bromo-2-methyl-propionate;

while the $R_1$, $R_2$ and Ar are defined as formula I.

4. The compound of claim 1, wherein the formula II of claim 1 is prepared as following: nucleophilic substitution of 4-chloro-3-nitropyridine (b1) with 4-cyclopropylnaphthalen-1-amine gave afforded the intermediate b2, which afforded P1-P8 via similar procedures to those shown in scheme 1, -continued

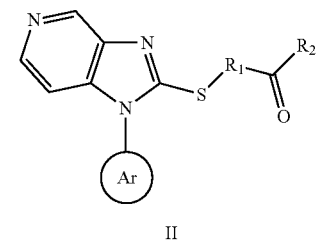

II (vii) NaHCO₃, EtOH, 60° C.; (ii) Pd/C, H₂, EtOH; (iii) EtOCS₂K, NaHCO₃, H₂O, EtOH; (iv) ester, K₂CO₃, DMF; (v) LiOH, THF, EtOH;

wherein, the ester is selected from ethyl 4-bromobutyrate, ethyl 2-chloropropionate or ethyl 2-bromo-2-methyl-propionate;

while the $R_1$, $R_2$ and Ar are defined as formula II.

5. The compound of claim 1, wherein the formula III of claim 1 is prepared as following: 3-chloro-2-nitropyridine (c1) was treated with 4-cyclopropyl-1-naphthylamine to afford intermediate c2 via Buchwald-Hartwig coupling reaction, then, reduction in the presence of Pd/C gave c3, which was cyclized with 1,1'-thiocarbonyldiimidazole to give the key intermediate c4, followed by nucleophilic substitution and hydrolysis to provide T1-T8.

scheme 3. synthetic route to 1H-imidazole [4,5-b]pyridine derivatives

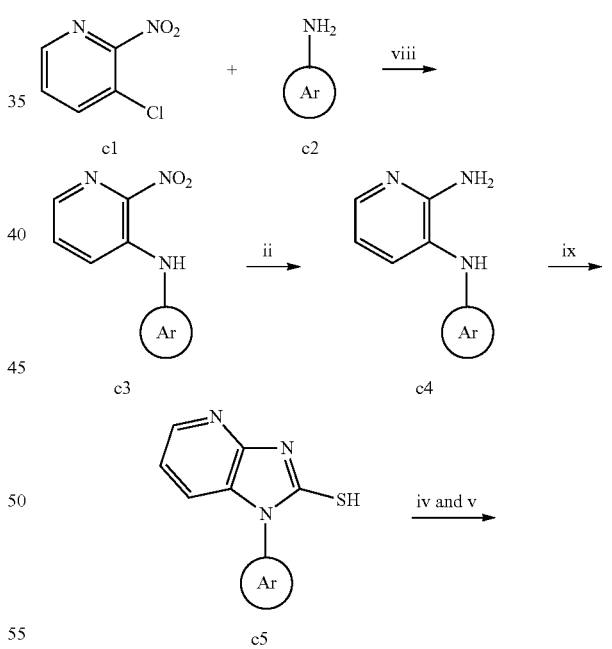

scheme 2. Synthetic route to 1H-imidazole[4,5-c]pyridine derivatives

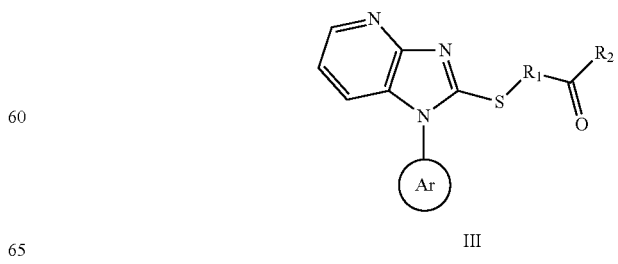

wherein, the ester is selected from ethyl 4-bromobutyrate, ethyl 2-chloropropionate or ethyl 2-bromo-2-methyl-propionate;

wherein, the room temperature is represented 20-30° C.;

while the $R_1$, $R_2$ and Ar are defined as formula III.

6. A process for treating an arthritis comprising a step of administrating to a subject in need a therapeutically effective amount of the compound of claim 1 or its pharmaceutically acceptable salt; said arthritis is a gout.

7. A pharmaceutical composition comprising a therapeutically effective amount of the compound of claim 1, one or more pharmaceutical acceptable carrier or excipient.

* * * * *